US006365386B1

(12) United States Patent
Hoshino et al.

(10) Patent No.: US 6,365,386 B1
(45) Date of Patent: Apr. 2, 2002

(54) ASTAXANTHIN SYNTHASE

(75) Inventors: Tatsuo Hoshino, Kamakura; Kazuyuki Ojima; Yutaka Setoguchi, both of Fujisawa, all of (JP)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/518,386

(22) Filed: Mar. 3, 2000

(30) Foreign Application Priority Data

Mar. 9, 1999 (EP) .............................. 99104668
Feb. 1, 2000 (EP) .............................. 00101666

(51) Int. Cl.[7] .............................. C12N 9/00; C12N 1/20; C12N 15/00; C12Q 1/68; C07H 21/04
(52) U.S. Cl. .................... 435/183; 435/6; 435/252.3; 435/320.1; 536/23.2
(58) Field of Search ............... 536/23.2; 435/252.3, 435/320.1, 183, 6

(56) References Cited

FOREIGN PATENT DOCUMENTS

EP         0 769 551 A1     4/1997
WO         WO 97/23633      7/1997

OTHER PUBLICATIONS

Martinez, et al., "Genetic transformation of astaxanthin mutants of *Phaffia rhodozyma*," Antonie van Leeuwenhoek, vol. 73: pp. 147–153 (1998).
Wery, et al., "High copy number integration into the ribosomal DNA of the yeast *Phaffia rhodozyma*," Gene, vol. 184, pp. 89–97 (1997).

*Primary Examiner*—Rebecca E. Prouty
*Assistant Examiner*—Maryam Monshipouri
(74) *Attorney, Agent, or Firm*—Bryan Cave LLP

(57) ABSTRACT

The present invention is directed to genetic materials useful for the preparation of astaxanthin from beta-carotene, such as polypeptides having astaxanthin synthase activity, DNA fragments coding for astaxanthin synthase, recombinant organisms and the like. Those novel genetic materials may be derived from *Phaffia rhodozyma*. The present invention also provides a process for the production of astaxanthin.

22 Claims, 3 Drawing Sheets

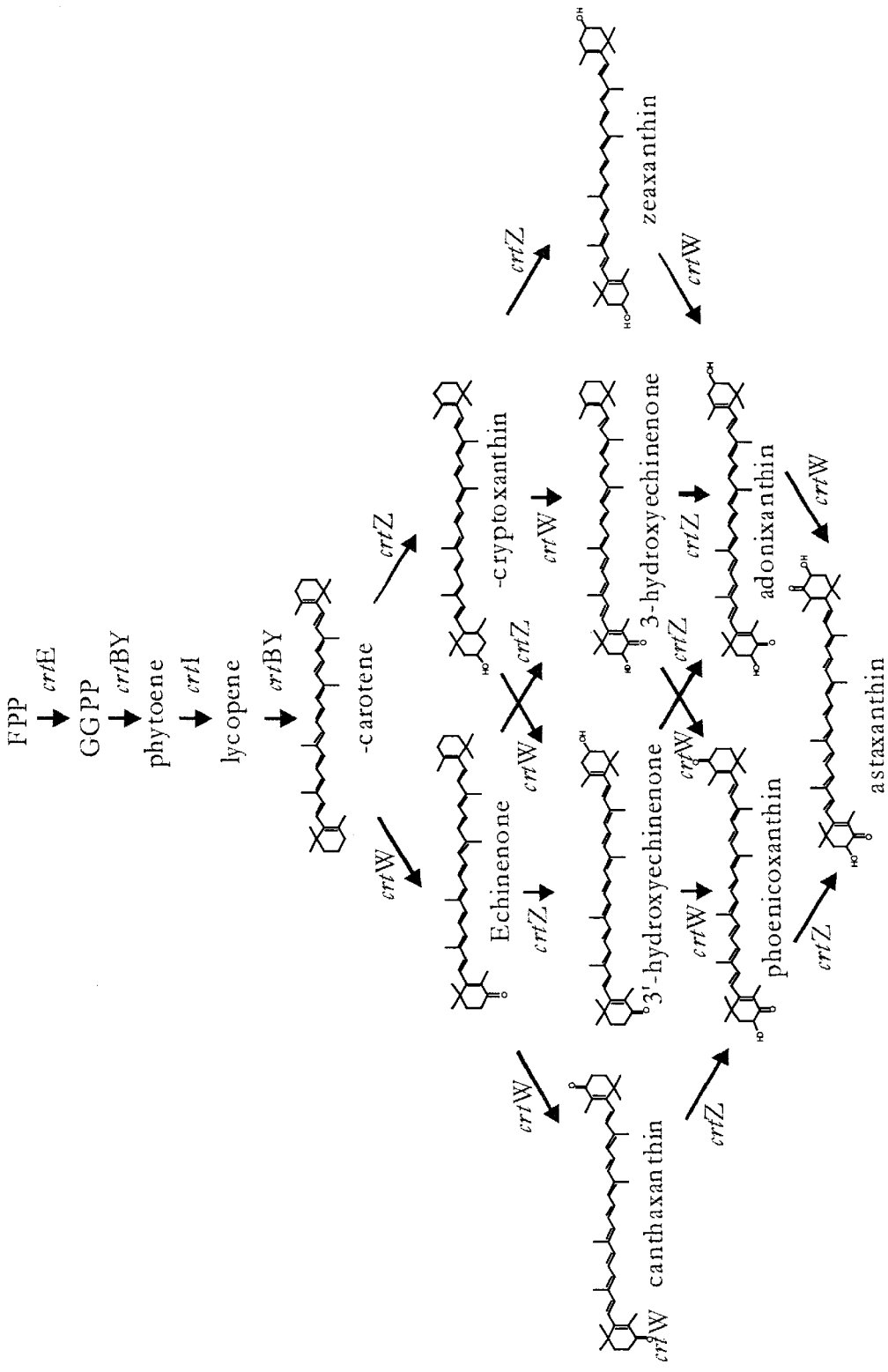
FIG.1 Biosynthetic pathway from GGPP to astaxanthin in the bacterial sytem which produces astaxanthin

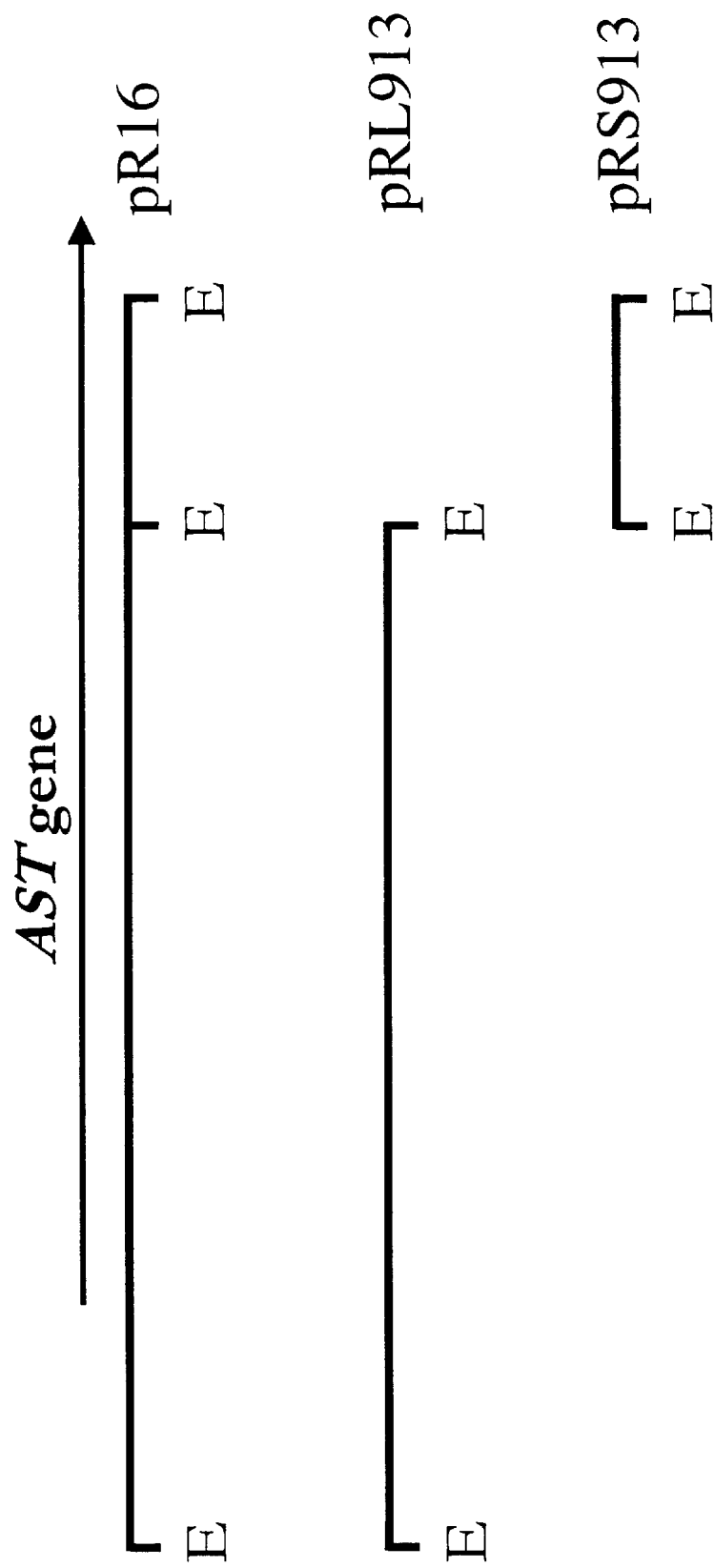
FIG. 2 Restriction map of DNA fragments which were used for functional analysis of *AST* gene from *Phaffia rhodozyma*.
Vector backbone of these plasmids was pUC-G418. Restriction enzyme indicated as E is *EcoRI*.

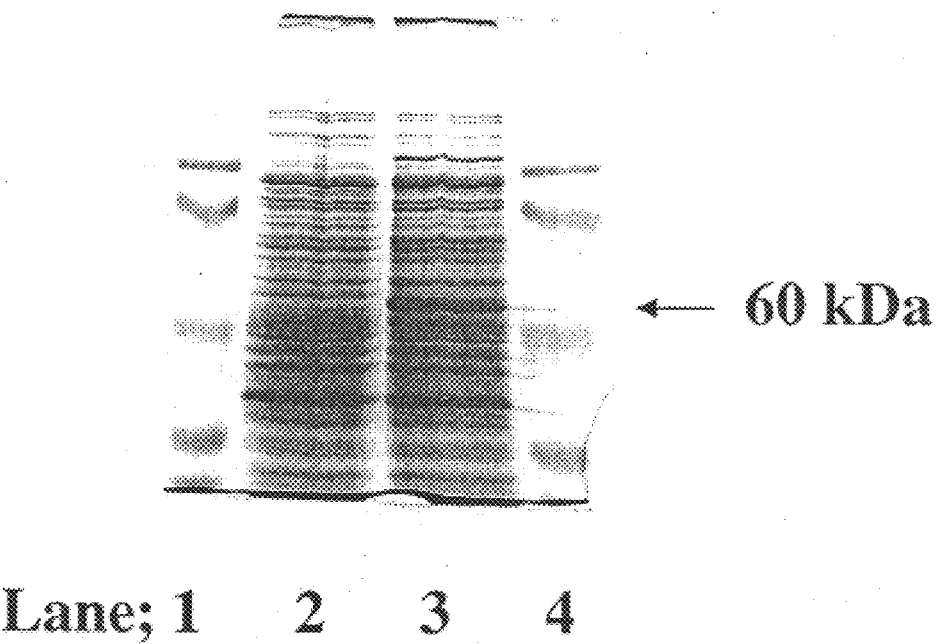
FIG. 3 Expression of *AST* gene in *E. coli*

SEQUENCE LISTING

<160> NUMBER OF SEQ ID NOS: 32

<210> SEQ ID NO 1
<211> LENGTH: 557
<212> TYPE: PRT
<213> ORGANISM: Phaffia rhodozyma
<220> FEATURE:

-continued

```
<221> NAME/KEY: TRANSIT
<222> LOCATION: (1)..(26)

<400> SEQUENCE: 1

Met Phe Ile Leu Val Leu Leu Thr Gly Ala Leu Gly Leu Ala Ala Phe
 1               5                  10                  15

Ser Trp Ala Ser Ile Ala Phe Phe Ser Leu Tyr Leu Ala Pro Arg Arg
            20                  25                  30

Ser Ser Leu Tyr Asn Leu Gln Gly Pro Asn His Thr Asn Tyr Phe Thr
        35                  40                  45

Gly Asn Phe Leu Asp Ile Leu Ser Ala Arg Thr Gly Glu Glu His Ala
    50                  55                  60

Lys Tyr Arg Glu Lys Tyr Gly Ser Thr Leu Arg Phe Ala Gly Ile Ala
65                  70                  75                  80

Gly Ala Pro Val Leu Asn Ser Thr Asp Pro Lys Val Phe Asn His Val
                85                  90                  95

Met Lys Glu Ala Tyr Asp Tyr Pro Lys Pro Gly Met Ala Ala Arg Val
            100                 105                 110

Leu Arg Ile Ala Thr Gly Asp Gly Val Val Thr Ala Glu Gly Glu Ala
        115                 120                 125

His Lys Arg His Arg Arg Ile Met Ile Pro Ser Leu Ser Ala Gln Ala
    130                 135                 140

Val Lys Ser Met Val Pro Ile Phe Leu Glu Lys Gly Met Glu Leu Val
145                 150                 155                 160

Asp Lys Met Met Glu Asp Ala Ala Glu Lys Asp Met Ala Val Gly Glu
                165                 170                 175

Ser Ala Gly Glu Lys Lys Ala Thr Arg Leu Glu Thr Glu Gly Val Asp
            180                 185                 190

Val Lys Asp Trp Val Gly Arg Ala Thr Leu Asp Val Met Ala Leu Ala
        195                 200                 205

Gly Phe Asp Tyr Lys Ser Asp Ser Leu Gln Asn Lys Thr Asn Glu Leu
    210                 215                 220

Tyr Val Ala Phe Val Gly Leu Thr Asp Gly Phe Ala Pro Thr Leu Asp
225                 230                 235                 240

Ser Phe Lys Ala Ile Met Trp Asp Phe Val Pro Tyr Phe Arg Thr Met
                245                 250                 255

Lys Arg Arg His Glu Ile Pro Leu Thr Gln Gly Leu Ala Val Ser Arg
            260                 265                 270

Arg Val Gly Ile Glu Leu Met Glu Gln Lys Gln Ala Val Leu Gly
        275                 280                 285

Ser Ala Ser Asp Gln Ala Val Asp Lys Lys Asp Val Gln Gly Arg Asp
    290                 295                 300

Ile Leu Ser Leu Leu Val Arg Ala Asn Ile Ala Ala Asn Leu Pro Glu
305                 310                 315                 320

Ser Gln Lys Leu Ser Asp Glu Val Leu Ala Gln Ile Ser Asn Leu
                325                 330                 335

Leu Phe Ala Gly Tyr Glu Thr Ser Thr Val Leu Thr Trp Met Phe
            340                 345                 350

His Arg Leu Ser Glu Asp Lys Ala Val Gln Asp Lys Leu Arg Glu Glu
        355                 360                 365

Ile Cys Gln Ile Asp Thr Asp Met Pro Thr Leu Asp Glu Leu Asn Ala
    370                 375                 380

Leu Pro Tyr Leu Glu Ala Phe Val Lys Glu Ser Leu Arg Leu Asp Pro
385                 390                 395                 400
```

-continued

```
Pro Ser Pro Tyr Ala Asn Arg Glu Cys Leu Lys Asp Glu Asp Phe Ile
            405                 410                 415
Pro Leu Ala Glu Pro Val Ile Gly Arg Asp Gly Ser Val Ile Asn Glu
        420                 425                 430
Val Arg Ile Thr Lys Gly Thr Met Val Met Leu Pro Leu Phe Asn Ile
            435                 440                 445
Asn Arg Ser Lys Phe Ile Tyr Gly Glu Asp Ala Glu Phe Arg Pro
    450                 455                 460
Glu Arg Trp Leu Glu Asp Val Thr Asp Ser Leu Asn Ser Ile Glu Ala
465                 470                 475                 480
Pro Tyr Gly His Gln Ala Ser Phe Ile Ser Gly Pro Arg Ala Cys Phe
                485                 490                 495
Gly Trp Arg Phe Ala Val Ala Glu Met Lys Ala Phe Leu Phe Val Thr
            500                 505                 510
Leu Arg Arg Val Gln Phe Glu Pro Ile Ile Ser His Pro Glu Tyr Glu
            515                 520                 525
His Ile Thr Leu Ile Ile Ser Arg Pro Arg Ile Val Gly Arg Glu Lys
        530                 535                 540
Glu Gly Tyr Gln Met Arg Leu Gln Val Lys Pro Val Glu
545                 550                 555
```

<210> SEQ ID NO 2
<211> LENGTH: 1932
<212> TYPE: DNA
<213> ORGANISM: Phaffia rhodozyma
<220> FEATURE:
<221> NAME/KEY: CDS
<222> LOCATION: (33)..(1706)
<221> NAME/KEY: polyA_site
<222> LOCATION: (1871)
<221> NAME/KEY: mRNA
<222> LOCATION: (14)..(1891)

<400> SEQUENCE: 2

```
gaattcggca cgaggccacc tactttctcc at atg ttc atc ttg gtc ttg ctc         53
                                   Met Phe Ile Leu Val Leu Leu
                                     1               5 aca ggt gct tta ggc ctg gct gct ttc tca tgg gca tcc ata gcg ttc        101
Thr Gly Ala Leu Gly Leu Ala Ala Phe Ser Trp Ala Ser Ile Ala Phe
        10                  15                  20 ttc agt ctt tac ctc gct ccg agg cga tct tca ctg tat aac ctt cag        149
Phe Ser Leu Tyr Leu Ala Pro Arg Arg Ser Ser Leu Tyr Asn Leu Gln
    25                  30                  35 ggc ccg aat cat acc aac tac ttt aca ggc aat ttt tta gac atc ctc        197
Gly Pro Asn His Thr Asn Tyr Phe Thr Gly Asn Phe Leu Asp Ile Leu
40                  45                  50                  55 tca gct cgt aca ggt gaa gag cat gcg aag tac aga gaa aaa tac gga        245
Ser Ala Arg Thr Gly Glu Glu His Ala Lys Tyr Arg Glu Lys Tyr Gly
                60                  65                  70 agc acc ctc cgg ttt gct ggg atc gct gga gca ccc gtc ttg aac tcg        293
Ser Thr Leu Arg Phe Ala Gly Ile Ala Gly Ala Pro Val Leu Asn Ser
            75                  80                  85 acc gat ccg aaa gtc ttc aac cat gtg atg aaa gaa gcc tac gac tat        341
Thr Asp Pro Lys Val Phe Asn His Val Met Lys Glu Ala Tyr Asp Tyr
        90                  95                 100 ccg aaa cct ggt atg gcc gct cga gtg ctc aga att gct acc gga gat        389
Pro Lys Pro Gly Met Ala Ala Arg Val Leu Arg Ile Ala Thr Gly Asp
    105                 110                 115 ggt gtt gtt acg gcg gaa ggt gaa gct cat aag cga cat cga agg atc        437
```

```
Gly Val Val Thr Ala Glu Gly Glu Ala His Lys Arg His Arg Arg Ile
120                 125                 130                 135 atg atc ccc tct ctg tcc gct cag gcc gtt aag tcg atg gtc cca att       485
Met Ile Pro Ser Leu Ser Ala Gln Ala Val Lys Ser Met Val Pro Ile
                140                 145                 150 ttc tta gaa aaa ggt atg gaa ctt gtc gac aag atg atg gag gat gcg       533
Phe Leu Glu Lys Gly Met Glu Leu Val Asp Lys Met Met Glu Asp Ala
            155                 160                 165 gct gag aag gat atg gcc gtg gga gag tcg gcc ggt gaa aag aag gca       581
Ala Glu Lys Asp Met Ala Val Gly Glu Ser Ala Gly Glu Lys Lys Ala
        170                 175                 180 acc aga ctc gag acc gaa gga gtc gat gta aag gat tgg gtc ggt cga       629
Thr Arg Leu Glu Thr Glu Gly Val Asp Val Lys Asp Trp Val Gly Arg
    185                 190                 195 gct act ctg gac gtc atg gct ctt gca gga ttt gac tat aag agc gac       677
Ala Thr Leu Asp Val Met Ala Leu Ala Gly Phe Asp Tyr Lys Ser Asp
200                 205                 210                 215 tcg ctc cag aac aag acc aat gag ctc tat gtc gct ttt gtc gga ctt       725
Ser Leu Gln Asn Lys Thr Asn Glu Leu Tyr Val Ala Phe Val Gly Leu
                220                 225                 230 acc gat ggg ttt gct cct acc ttg gac tcg ttc aag gct atc atg tgg       773
Thr Asp Gly Phe Ala Pro Thr Leu Asp Ser Phe Lys Ala Ile Met Trp
            235                 240                 245 gat ttt gta cct tac ttc cga act atg aaa cgg aga cat gag ata cct       821
Asp Phe Val Pro Tyr Phe Arg Thr Met Lys Arg Arg His Glu Ile Pro
        250                 255                 260 ttg act caa gga tta gca gtt tcc cga cga gtt ggg atc gag ctt atg       869
Leu Thr Gln Gly Leu Ala Val Ser Arg Arg Val Gly Ile Glu Leu Met
    265                 270                 275 gag caa aag aag cag gcc gtg ctt ggc tca gct tcc gat cag gct gtt       917
Glu Gln Lys Lys Gln Ala Val Leu Gly Ser Ala Ser Asp Gln Ala Val
280                 285                 290                 295 gat aaa aag gat gtt caa ggt cgg gat atc cta agt ctc cta gtg aga       965
Asp Lys Lys Asp Val Gln Gly Arg Asp Ile Leu Ser Leu Leu Val Arg
                300                 305                 310 gca aac atc gcc gcc aac ctg cct gaa tct caa aag ctg tcc gat gag      1013
Ala Asn Ile Ala Ala Asn Leu Pro Glu Ser Gln Lys Leu Ser Asp Glu
            315                 320                 325 gag gta ctc gct cag atc agt aac ctg tta ttt gct gga tat gaa act      1061
Glu Val Leu Ala Gln Ile Ser Asn Leu Leu Phe Ala Gly Tyr Glu Thr
        330                 335                 340 tct tcg aca gtc ttg aca tgg atg ttt cac cga ctc tca gaa gac aaa      1109
Ser Ser Thr Val Leu Thr Trp Met Phe His Arg Leu Ser Glu Asp Lys
    345                 350                 355 gcc gtt cag gat aaa ctt cga gaa gaa att tgt cag atc gac acg gat      1157
Ala Val Gln Asp Lys Leu Arg Glu Glu Ile Cys Gln Ile Asp Thr Asp
360                 365                 370                 375 atg cct acg cta gac gaa ctt aat gcg ttg cct tat ctc gaa gcg ttt      1205
Met Pro Thr Leu Asp Glu Leu Asn Ala Leu Pro Tyr Leu Glu Ala Phe
                380                 385                 390 gtt aag gag tct ctt cgt cta gac cct cct agt ccg tat gct aac cgt      1253
Val Lys Glu Ser Leu Arg Leu Asp Pro Pro Ser Pro Tyr Ala Asn Arg
            395                 400                 405 gaa tgc tta aag gat gaa gac ttc atc cca ctt gcc gag cct gtc att      1301
Glu Cys Leu Lys Asp Glu Asp Phe Ile Pro Leu Ala Glu Pro Val Ile
        410                 415                 420 ggt cga gat ggg tcg gtc atc aac gag gtc cgg atc acg aaa gga acg      1349
Gly Arg Asp Gly Ser Val Ile Asn Glu Val Arg Ile Thr Lys Gly Thr
    425                 430                 435
```

```
atg gtc atg ctt ccg ttg ttc aac atc aat cgt tca aag ttc att tat      1397
Met Val Met Leu Pro Leu Phe Asn Ile Asn Arg Ser Lys Phe Ile Tyr
440                 445                 450                 455 gga gaa gat gca gaa gaa ttc aga ccg gag agg tgg ctt gag gac gta      1445
Gly Glu Asp Ala Glu Glu Phe Arg Pro Glu Arg Trp Leu Glu Asp Val
                460                 465                 470 aca gac tcg ctc aac agt att gaa gca ccc tat gga cac cag gcg agc      1493
Thr Asp Ser Leu Asn Ser Ile Glu Ala Pro Tyr Gly His Gln Ala Ser
            475                 480                 485 ttt atc tct gga ccc aga gct tgc ttt ggt tgg cga ttt gct gtc gcc      1541
Phe Ile Ser Gly Pro Arg Ala Cys Phe Gly Trp Arg Phe Ala Val Ala
        490                 495                 500 gag atg aag gcc ttc ttg ttt gtc act ctc cgt cgg gtc cag ttc gag      1589
Glu Met Lys Ala Phe Leu Phe Val Thr Leu Arg Arg Val Gln Phe Glu
    505                 510                 515 ccc atc atc tct cat cca gag tac gag cac atc acc ttg atc att tcc      1637
Pro Ile Ile Ser His Pro Glu Tyr Glu His Ile Thr Leu Ile Ile Ser
520                 525                 530                 535 cgt cct cga atc gtt ggt aga gag aag gag ggg tac cag atg cgt ttg      1685
Arg Pro Arg Ile Val Gly Arg Glu Lys Glu Gly Tyr Gln Met Arg Leu
                540                 545                 550 cag gtc aag ccg gtc gaa tga gttgattctt catatgttaa gagaagttct         1736
Gln Val Lys Pro Val Glu
            555 atatctgaga atgtgtgact aggacaatgc cttctttgta tcgatttgtt tctcataccc    1796 gggcaggcgc tatgacttct acgtcgtcta tcgtcgctct ggactctctt cttaccctat    1856 atattattcc atccgaaaaa aaaaaaaaaa aaaaaaaaaa aaaagcggc cgctcgagcc     1916 ggctcgtgcc gaattc                                                    1932

<210> SEQ ID NO 3
<211> LENGTH: 557
<212> TYPE: PRT
<213> ORGANISM: Phaffia rhodozyma

<400> SEQUENCE: 3

Met Phe Ile Leu Val Leu Leu Thr Gly Ala Leu Gly Leu Ala Ala Phe
1               5                   10                  15

Ser Trp Ala Ser Ile Ala Phe Phe Ser Leu Tyr Leu Ala Pro Arg Arg
            20                  25                  30

Ser Ser Leu Tyr Asn Leu Gln Gly Pro Asn His Thr Asn Tyr Phe Thr
        35                  40                  45

Gly Asn Phe Leu Asp Ile Leu Ser Ala Arg Thr Gly Glu Glu His Ala
    50                  55                  60

Lys Tyr Arg Glu Lys Tyr Gly Ser Thr Leu Arg Phe Ala Gly Ile Ala
65                  70                  75                  80

Gly Ala Pro Val Leu Asn Ser Thr Asp Pro Lys Val Phe Asn His Val
                85                  90                  95

Met Lys Glu Ala Tyr Asp Tyr Pro Lys Pro Gly Met Ala Ala Arg Val
            100                 105                 110

Leu Arg Ile Ala Thr Gly Asp Gly Val Val Thr Ala Glu Gly Glu Ala
        115                 120                 125

His Lys Arg His Arg Arg Ile Met Ile Pro Ser Leu Ser Ala Gln Ala
    130                 135                 140

Val Lys Ser Met Val Pro Ile Phe Leu Glu Lys Gly Met Glu Leu Val
145                 150                 155                 160

Asp Lys Met Met Glu Asp Ala Ala Glu Lys Asp Met Ala Val Gly Glu
```

```
                165                 170                 175
Ser Ala Gly Glu Lys Lys Ala Thr Arg Leu Glu Thr Glu Gly Val Asp
                180                 185                 190

Val Lys Asp Trp Val Gly Arg Ala Thr Leu Asp Val Met Ala Leu Ala
            195                 200                 205

Gly Phe Asp Tyr Lys Ser Asp Ser Leu Gln Asn Lys Thr Asn Glu Leu
        210                 215                 220

Tyr Val Ala Phe Val Gly Leu Thr Asp Gly Phe Ala Pro Thr Leu Asp
225                 230                 235                 240

Ser Phe Lys Ala Ile Met Trp Asp Phe Val Pro Tyr Phe Arg Thr Met
                245                 250                 255

Lys Arg Arg His Glu Ile Pro Leu Thr Gln Gly Leu Ala Val Ser Arg
            260                 265                 270

Arg Val Gly Ile Glu Leu Met Glu Gln Lys Lys Gln Ala Val Leu Gly
        275                 280                 285

Ser Ala Ser Asp Gln Ala Val Asp Lys Lys Asp Val Gln Gly Arg Asp
    290                 295                 300

Ile Leu Ser Leu Leu Val Arg Ala Asn Ile Ala Ala Asn Leu Pro Glu
305                 310                 315                 320

Ser Gln Lys Leu Ser Asp Glu Glu Val Leu Ala Gln Ile Ser Asn Leu
                325                 330                 335

Leu Phe Ala Gly Tyr Glu Thr Ser Ser Thr Val Leu Thr Trp Met Phe
            340                 345                 350

His Arg Leu Ser Glu Asp Lys Ala Val Gln Asp Lys Leu Arg Glu Glu
        355                 360                 365

Ile Cys Gln Ile Asp Thr Asp Met Pro Thr Leu Asp Glu Leu Asn Ala
    370                 375                 380

Leu Pro Tyr Leu Glu Ala Phe Val Lys Glu Ser Leu Arg Leu Asp Pro
385                 390                 395                 400

Pro Ser Pro Tyr Ala Asn Arg Glu Cys Leu Lys Asp Glu Asp Phe Ile
                405                 410                 415

Pro Leu Ala Glu Pro Val Ile Gly Arg Asp Gly Ser Val Ile Asn Glu
            420                 425                 430

Val Arg Ile Thr Lys Gly Thr Met Val Met Leu Pro Leu Phe Asn Ile
        435                 440                 445

Asn Arg Ser Lys Phe Ile Tyr Gly Glu Asp Ala Glu Glu Phe Arg Pro
    450                 455                 460

Glu Arg Trp Leu Glu Asp Val Thr Asp Ser Leu Asn Ser Ile Glu Ala
465                 470                 475                 480

Pro Tyr Gly His Gln Ala Ser Phe Ile Ser Gly Pro Arg Ala Cys Phe
                485                 490                 495

Gly Trp Arg Phe Ala Val Ala Glu Met Lys Ala Phe Leu Phe Val Thr
            500                 505                 510

Leu Arg Arg Val Gln Phe Glu Pro Ile Ile Ser His Pro Glu Tyr Glu
        515                 520                 525

His Ile Thr Leu Ile Ile Ser Arg Pro Arg Ile Val Gly Arg Glu Lys
    530                 535                 540

Glu Gly Tyr Gln Met Arg Leu Gln Val Lys Pro Val Glu
545                 550                 555

<210> SEQ ID NO 4
<211> LENGTH: 3969
<212> TYPE: DNA
<213> ORGANISM: Phaffia rhodozyma
```

-continued

```
<220> FEATURE:
<221> NAME/KEY: 5'UTR
<222> LOCATION: (517)..(518)
<221> NAME/KEY: intron
<222> LOCATION: (784)..(898)
<221> NAME/KEY: intron
<222> LOCATION: (1016)..(1087)
<221> NAME/KEY: intron
<222> LOCATION: (1180)..(1302)
<221> NAME/KEY: intron
<222> LOCATION: (1518)..(1600)
<221> NAME/KEY: intron
<222> LOCATION: (1635)..(1723)
<221> NAME/KEY: intron
<222> LOCATION: (1867)..(1939)
<221> NAME/KEY: intron
<222> LOCATION: (2000)..(2081)
<221> NAME/KEY: intron
<222> LOCATION: (2182)..(2257)
<221> NAME/KEY: intron
<222> LOCATION: (2355)..(2431)
<221> NAME/KEY: intron
<222> LOCATION: (2543)..(2618)
<221> NAME/KEY: intron
<222> LOCATION: (2653)..(2742)
<221> NAME/KEY: intron
<222> LOCATION: (2815)..(2962)
<221> NAME/KEY: intron
<222> LOCATION: (3051)..(3113)
<221> NAME/KEY: intron
<222> LOCATION: (3172)..(3247)
<221> NAME/KEY: intron
<222> LOCATION: (3322)..(3398)
<221> NAME/KEY: intron
<222> LOCATION: (3424)..(3513)
<221> NAME/KEY: polyA_site
<222> LOCATION: (3865)..(3866)
<221> NAME/KEY: intron
<222> LOCATION: (653)..(734)

<400> SEQUENCE: 4
cggaccgaag cctcgccagc agttgatcaa gcgaaccaag ccgaacaatc ctggcgcgcc      60
tggaggagcg ggagcgggag gagcagcagg tgatgcatcg ggtggacaga atcagtagtg     120
tgtgtgtatg tgtgtagtgt agttgggttg tcccatgtgc ttcttcttat catcatcatt     180
tctttaaaat ctctacattg aatgtttacc ggaacgggct tgatgatac tacggaccac      240
gttgtgtaac cagttcgatt gagattacga ttagatagcc gatccgtcga tcagatctcg     300
atctagagcg acatctggct cgatcggtcc ttgccgaaaa tcagggcacc gatcagggca     360
gaggaacgcc gaggccgaac gagacagaca caccatcatc atcagccatg tctttttgt      420
gatcgttttt acatactacc cgtcgattct aaccttcttt cttcttctct tgccatcttt     480
gcattctcta tctcgtgtaa catcgatccg attcttgcca cctactttct ccatatgttc     540
atcttggtct tgctcacagg tgctttaggc ctggctgctt tctcatgggc atccatagcg     600
ttcttcagtc tttacctcgc tccgaggcga tcttcactgt ataaccttca gggtaagaat     660
tgagctctgg aatcatgctt gtgtaaatcc tataatctca ttcatcctat tcctcttctt     720
catcctctct tcaggcccga atcataccaa ctactttaca ggcaattttt tagacatcct     780
ctcgtgagtt ttcatcattg gctcagtcgt ccaatcttaa cgatcatcgc taacgacctt     840
tcggacgcgt tcttctttct atgtgaaatc tgatctttgg tttgttacga gagcacagag     900
ctcgtacagg tgaagagcat gcgaagtaca gagaaaaata cggaagcacc ctccggtttg     960
ctgggatcgc tggagcaccc gtcttgaact cgaccgatcc gaaagtcttc aaccagtttg    1020
tccatccgaa ccctcatcct cctctgctga tcaattcaac tgtagttaac gcactttgaa    1080
tggacagtgt gatgaaagaa gcctacgact atccgaaacc tggtatggcc gctcgagtgc    1140
```

```
tcagaattgc taccggagat ggtgttgtta cggcggaagg tgcttttcaa gttctcttat    1200
atcacatcta atccactcgg cgcgattgaa ctcaacattt ctgacgagcc tgtcaccttg    1260
ttttcacttc atggtctcgg tgcatcttgt ctcatctcat aggtgaagct cataagcgac    1320
atcgaaggat catgatcccc tctctgtccg ctcaggccgt taagtcgatg gtcccaattt    1380
tcttagaaaa aggtatggaa cttgtcgaca agatgatgga ggatgcggct gagaaggata    1440
tggccgtggg agagtcggcc ggtgaaaaga aggcaaccag actcgagacc gaaggagtcg    1500
atgtaaagga ttgggtcgtg agtacccgcc tattccttca ccttgatgga cgaagcatat    1560
caaggaaagg ttcattgact gacaaacact atcttaccag ggtcgagcta ctctggacgt    1620
catggctctt gcaggtcagt ctactctctc ttataaatgc tccacatatg tatgcatgta    1680
ctgacatgct cttcctatat tcgatacgac gtcatatgtc caggatttga ctataagagc    1740
gactcgctcc agaacaagac caatgagctc tatgtcgctt ttgtcggact taccgatggg    1800
tttgctccta ccttggactc gttcaaggct atcatgtggg attttgtacc ttacttccga    1860
actatggtat gtctgccatt cttgatatc caaagattat ggataggtta cttgctaaaa     1920
tttcacctat cgtgaacaga acggagaca tgagatacct ttgactcaag gattagcagt     1980
ttcccgacga gttgggatcg taagtgccag atcaagcctc tctgaatatt cttggtcatc    2040
atcttaacct cctaggctca ttcatccatg gtgcgcaata ggagcttatg gagcaaaaga    2100
agcaggccgt gcttggctca gcttccgatc aggctgttga taaaaaggat gttcaaggtc    2160
gggatatcct aagtctccta ggttagtaac gttttttaaac gtatatacag agcggcgaca    2220 ttcttttccct gacaactgtc aacatgctcg ttactagtga gagcaaacat cgccgccaac    2280
ctgcctgaat ctcaaaagct gtccgatgag gaggtactcg ctcagatcag taacctgtta    2340
tttgctggat atgagtgtgt atccttttccc ctctctatcc ttagctgatt aaaagcacta    2400
atagaggtct ttatgtttcc tgtttgatca gaacttcttc gacagtcttg acatggatgt    2460
ttcaccgact ctcagaagac aaagccgttc aggataaact tcgagaagaa atttgtcaga    2520
tcgacacgga tatgcctacg ctgtgaggat gtttttgatg ctaaattact tcttcttgca    2580
aatgactaaa acggccttcc attcttgatc cattttagag acgaacttaa tgcgttgcct    2640
tatctcgaag cggttggttc tcgattcttg gtcttgtctt ccaaatacaa tacggattat    2700
tgctcatctg atttgcgtct acgggctgtg gaatttaact agtttgttaa ggagtctctt    2760
cgtctagacc ctcctagtcc gtatgctaac cgtgaatgct taaaggatga agacgtatgt    2820
tggcttcatc acgcataatt ttcatttcat attcctttgt acatacgcat acaggctgac    2880
cgagctcaaa ttccggcttc ctcttctgtg cttcttttc tggcctttct tatcttcatt     2940
cttcaaccaa aatttgtcac agttcatccc acttgccgag cctgtcattg gtcgagatgg    3000
gtcggtcatc aacgaggtcc ggatcacgaa aggaacgatg gtcatgcttc gtaagttttc    3060
ctttatttca tctcgtccat gaaatagttt ctgatagacg cggaccaatt cagcgttgtt    3120
caacatcaat cgttcaaagt tcatttatgg agaaagatgca gaagaattca ggtacaattc    3180
gttttctttt aaaagccaat cggtttcgta tcgtaattga ccgggctctc ttttaatttc    3240
tcgaaagacc ggagaggtgg cttgaggacg taacagactc gctcaacagt attgaagcac    3300
cctatggaca ccaggcgagc tgtatgtttt attgatttta tctttgtgaa ttttgcaaaa    3360
cgttgaactt cgcgcttccc ttgttgttga aatcccagtt atctctggac ccagagcttg    3420
cttgtaagtt tcttctcatc tggcgcctta gcagtatccg atcagccatc tagttctttg    3480
```

-continued

```
tacgattgtt tctgactctc tcgactttcg cagtggttgg cgatttgctg tcgccgagat    3540
gaaggccttc ttgtttgtca ctctccgtcg ggtccagttc gagcccatca tctctcatcc    3600
agagtacgag cacatcacct tgatcatttc ccgtcctcga atcgttggta gagagaagga    3660
ggggtaccag atgcgtttgc aggtcaagcc ggtcgaatga gttgattctt catatgttaa    3720
gagaagttct atatctgaga atgtgtgact aggacaatgc cttctttgta tcgatttgtt    3780
tctcataccc gggcaggcgc tatgacttct acgtcgtcta tcgtcgctct ggactctctt    3840
cttaccctat atattattcc atccgtctgt atatttgtct atcacgacgt ctgtgtcgtc    3900
aactcaatat tcagcctctt catgcttctg tgtctccata gatgtgatct tcatgtttgt    3960
cgactgcag                                                            3969
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:
Sense primer for expression of the AST gene in E. coli

<400> SEQUENCE: 5

```
gttcaaagtt catttatgga                                                   20
```

<210> SEQ ID NO 6
<211> LENGTH: 47
<212> TYPE: DNA
<213> ORGANISM: Artificial Sequence
<220> FEATURE:
<223> OTHER INFORMATION: Description of Artificial Sequence: Antisense
primer for expession of the AST gene in E. coli

<400> SEQUENCE: 6

```
ggatcctcag tggtggtggt ggtggtgttc gaccggcttg acctgca                     47
```

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: 5' sense
primer for expression of a modified AST gene in E. coli

<400> SEQUENCE: 7

```
catatgcacc accaccacca ccacctgtat aaccttcagg ggccc                       45
```

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: 5'
antisense primer for expression of a modified AST gene in
E. coli

<400> SEQUENCE: 8

```
gtaacaacac catctccggt                                                   20
```

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: 3' anti
sense primer for expression of a modified AST gene in E. coli

<400> SEQUENCE: 9
ggatcctcaa ctcattcgac cggctt                                        26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Genome
      walking primer for cloning of the AST gene

<400> SEQUENCE: 10
tagagagaag gagggtacc agatgc                                         26

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Antisense
      primer for cloning of the terminator region of the AST gene

<400> SEQUENCE: 11
ccccggattg tggagaaact                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Sense
      primer for cloning the genomic AST gene

<400> SEQUENCE: 12
atgttcatct tggtcttgct                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Antisense
      primer for cloning the genomic AST gene

<400> SEQUENCE: 13
acgtagaagt catagcgcct                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Sense
      primer for RT-PCR of the AST gene

<400> SEQUENCE: 14
tttgactcaa ggattagcag                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Antisense
      primer for RT-PCR of the AST gene

```
<400> SEQUENCE: 15
tgtcttctga gagtcggtga                                                    20

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Degenerate
      sense primer for cloning of the TPI gene
<221> NAME/KEY: misc_feature
<222> LOCATION: 3
<223> OTHER INFORMATION: n is a or c or g or t
<221> NAME/KEY: misc_feature
<222> LOCATION: 6
<223> OTHER INFORMATION: n is a or c or g or t
<221> NAME/KEY: misc_feature
<222> LOCATION: 15
<223> OTHER INFORMATION: n is a or c or g or t
<221> NAME/KEY: misc_feature
<222> LOCATION: 18
<223> OTHER INFORMATION: n is a or c or g or t
<221> NAME/KEY: misc_feature
<222> LOCATION: 21
<223> OTHER INFORMATION: n is a or c or g or t

<400> SEQUENCE: 16
mgnacnttyt tygtnggngg naay                                               24

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Degenerate
      antisense primer for cloning the TPI gene
<221> NAME/KEY: misc_feature
<222> LOCATION: 3
<223> OTHER INFORMATION: n is a or c or g or t
<221> NAME/KEY: misc_feature
<222> LOCATION: 6
<223> OTHER INFORMATION: n is a or c or g or t
<221> NAME/KEY: misc_feature
<222> LOCATION: 9
<223> OTHER INFORMATION: n is a or c or g or t
<221> NAME/KEY: misc_feature
<222> LOCATION: 12
<223> OTHER INFORMATION: n is a or c or g or t
<221> NAME/KEY: misc_feature
<222> LOCATION: 18
<223> OTHER INFORMATION: n is a or c or g or t
<221> NAME/KEY: misc_feature
<222> LOCATION: 24
<223> OTHER INFORMATION: n is a or c or g or t

<400> SEQUENCE: 17
gcnccnccna cnarraancc rtcnacrtc                                          29

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Primary
      walking primer for cloning of the TPI terminator

<400> SEQUENCE: 18
gcttacctcg cttccaacgt ttcccag                                            27

<210> SEQ ID NO 19
<211> LENGTH: 27
```

```
<212> TYPE: DNA
<213> ORGANISM: Artificial Sequence
<220> FEATURE:
<223> OTHER INFORMATION: Description of Artificial Sequence: Nested
      walking primer for cloning of the TPI terminator

<400> SEQUENCE: 19
ggatctgtct ctgcctccaa ctgcaag                                        27

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Primary
      walking primer for cloning of the TPI promoter

<400> SEQUENCE: 20
gggtcaatgt cggcagcgag aagccca                                        27

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Nested
      walking primer for cloning of the TPI promoter

<400> SEQUENCE: 21
atgtactcgg tagcactgat caagtag                                        27

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Sense
      primer for construction of the TPI promoter cassette

<400> SEQUENCE: 22
gcggccgcat ccgtctcgcc atcagtct                                       28

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Antisense
      primer for construction of the TPI promoter cassette

<400> SEQUENCE: 23
cctgcaggtc tagagatgaa taaatataaa gagt                                34

<210> SEQ ID NO 24
<211> LENGTH: 34
<212> TYPE: DNA
<213> ORGANISM: Artificial Sequence
<220> FEATURE:
<223> OTHER INFORMATION: Description of Artificial Sequence: Sense
      primer for construction of the TPI terminator cassette

<400> SEQUENCE: 24
cctgcaggta aatatatcca gggattaacc ccta                                34

<210> SEQ ID NO 25
<211> LENGTH: 28
<212> TYPE: DNA
```

```
<213> ORGANISM: Artificial Sequence
<220> FEATURE:
<223> OTHER INFORMATION: Description of Artificial Sequence: Antisense
      primer for construction of the TPI terminator cassette

<400> SEQUENCE: 25
ggtacccgtg cgcagtcgac cgagacat                                          28

<210> SEQ ID NO 26
<211> LENGTH: 35
<212> TYPE: DNA
<213> ORGANISM: Artificial Sequence
<220> FEATURE:
<223> OTHER INFORMATION: Description of Artificial Sequence: Degenerate
      sense primer for cloning of the AMY gene
<221> NAME/KEY: misc_feature
<222> LOCATION: 15
<223> OTHER INFORMATION: n is a or c or g or t
<221> NAME/KEY: misc_feature
<222> LOCATION: 21
<223> OTHER INFORMATION: n is a or c or g or t
<221> NAME/KEY: misc_feature
<222> LOCATION: 27
<223> OTHER INFORMATION: n is a or c or g or t
<221> NAME/KEY: misc_feature
<222> LOCATION: 30
<223> OTHER INFORMATION: n is a or c or g or t

<400> SEQUENCE: 26
gaytayathc arggnatggg nttyrmngcn athtg                                  35

<210> SEQ ID NO 27
<211> LENGTH: 35
<212> TYPE: DNA
<213> ORGANISM: Artificial Sequence
<220> FEATURE:
<223> OTHER INFORMATION: Description of Artificial Sequence: Degenerate
      antisense primer for cloning of the AMY gene
<221> NAME/KEY: misc_feature
<222> LOCATION: 6
<223> OTHER INFORMATION: n is a or c or g or t
<221> NAME/KEY: misc_feature
<222> LOCATION: 9
<223> OTHER INFORMATION: n is a or c or g or t
<221> NAME/KEY: misc_feature
<222> LOCATION: 24
<223> OTHER INFORMATION: n is a or c or g or t
<221> NAME/KEY: misc_feature
<222> LOCATION: 30
<223> OTHER INFORMATION: n is a or c or g or t

<400> SEQUENCE: 27
tgytcngtnc crtartadat datnggdatn ccrtc                                  35

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Sense
      primer for construction of a partial AMY cassette

<400> SEQUENCE: 28
ccgcggcatt gatacctcta ccccgt                                            26

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Antisense
```

-continued

```
       primer for construction of a partial AMY cassette

<400> SEQUENCE: 29
gcggccgcct gcaatcctgg atccaccg                                         28

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Sense
      primer for construction of the AST cassette

<400> SEQUENCE: 30
tctagaatgt tcatcttggt cttgctca                                         28

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Antisense
      primer for construction of the AST cassette

<400> SEQUENCE: 31
cctgcaggtc attcgaccgg cttgacct                                         28

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Sense
      primer for confirmation of integration at the AMY locus
      by PCR analysis

<400> SEQUENCE: 32
ctctcctgtt cacaaaaaca                                                  20
```

ASTAXANTHIN SYNTHASE

The present invention relates to recombinant production of carotenoids and biological materials useful therefor.

Phaffia rhodozyma (P. rhodozyma) is a carotenogenic yeast strain which produces astaxanthin. Astaxanthin is distributed in a wide variety of organisms such as animals (birds such as flamingo and scarlet ibis, and fish such as rainbow trout and salmon), algae and microorganisms. It is also recognized that astaxanthin has a strong antioxidation property against oxygen radicals, and is expected to be useful pharmaceutically for protecting living cells against certain diseases, such as a cancer. Moreover, industrial need for astaxanthin as a coloring reagent is increasing, especially in the industry of farmed fish like salmon, because astaxanthin imparts a distinctive orange-red coloration to the animals and contributes to consumer appeal in the marketplace.

P. rhodozyma is known as a carotenogenic yeast strain which produces astaxanthin. Different from the other carotenogenic yeast, Rhodotorula species, P. rhodozyma can ferment some sugars such as D-glucose. This is an important feature from a viewpoint of industrial application. In a recent taxonomic study, a sexual cycle of P. rhodozyma was revealed and its telemorphic state was designated under the name of Xanthophyllomyces dendrorhous (W. I. Golubev; Yeast 11, 101–110, 1995). Some strain improvement studies to obtain hyper producers of astaxanthin from P. rhodozyma have been conducted, but such efforts have been restricted to employ the method of conventional mutagenesis and protoplast fusion in this decade. Recently, Wery et al. developed a host vector system using P. rhodozyma in which a non-replicable plasmid was integrated in multiple copies into the genome of the ribosomal DNA of P. rhodozyma (Wery et al., Gene, 184, 89–97, 1997). Verdoes et al. reported more improved vectors to obtain a transformant of P. rhodozyma as well as its three carotenogenic genes which code for the enzymes that catalyze the reactions from geranylgeranyl pyrophosphate to beta-carotene (WO 97/23633).

A specific biosynthetic pathway for carotenogenesis branches from the general isoprenoid pathway at the point of an important intermediate, farnesyl pyrophosphate (FPP) (FIG. 1). FPP and IPP are condensed by geranylgeranyl pyrophosphate (GGPP) synthase which is encoded by crtE in P. rhodozyma to produce GGPP. GGPP is then converted to beta-carotene by the sequential reaction of an enzyme functioning doubly as phytoene synthase and lycopene cyclase which is encoded by crtBY and phytoene desaturase encoded by crtI.

In bacteria, enzymes and genes which are involved in xanthophyll formation have been isolated and characterized in detail. Beta-carotene hydroxylase which is coded by crtZ is involved in the two steps of hydroxylation for the beta-ionone-ring of beta-carotene at both of the ends. The crtZ gene has been cloned from a wide variety of organisms such as Erwinia uredovora (Misawa et al., J. Bacteriol., 172, 6704–6712, 1990), Flavobactor species (L. Pasamontes et al., 185 (1), 35–41, 1997) and Agrobacterium aurantiacum (Misawa et al., J. Bacteriol., 177 (22), 6575–6584, 1995). Beta-carotene ketolase which is encoded by crtW catalyzes the two steps of introduction of an oxo-group into the beta-ionone -ring of beta-carotene at both of the ends. Kajiwara et al. cloned and sequenced the bkt gene corresponding to crtW in eubacteria from Haematococcus bluvialis (Kajiwara et al., P. Mol. Biol., 29, 343–352, 1995). Harker et al. also cloned and sequenced the crtO gene corresponding to crtW in eubacteria from Synechococcus PCC7942 (Harker et al., FEBS Letters, 404, 129–134, 1997). Both enzymes, i.e., the hydroxylase and the ketolase, have wide substrate specificity and this ensures the formation of a wide variety of xanthophylls in case both of the enzymes react at the same time, depending on the reaction condition. (FIG. 1)

As described above, all the genes which were involved in the formation of beta-carotene from FPP have been isolated but the enzymes and genes which would be involved in the last step of xanthophyll formation from beta-carotene have not been identified on the protein and DNA level in P.rhodozyma. Although Johnson et al. (Crit. Rev. Biotechnol, 11 (4), 297–326, 191) proposed the existence of two independent pathways for astaxanthin formation by assuming that some of the xanthophyll compounds isolated by them would be intermediates of astaxanthin biosynthesis, these two independent pathways could not be proven because enzymes and genes which are involved in such pathways could not be isolated. Furthermore, it can not be excluded that these xanthophyll compounds could have resulted from an experimental artifact in the isolation step of these compounds. Failure to isolate a mutant from P. rhodozyma which accumulates intermediates in the biosynthetic pathway from beta-carotene to astaxanthin made it difficult to clarify the biosynthetic pathway from beta-carotene to astaxanthin.

SUMMARY OF THE INVENTION

This invention relates to a gene and an enzyme which is involved in the last step of astaxanthin biosynthesis (i.e., from beta-carotene to astaxanthin).

The present invention provides an isolated DNA, for example, a cDNA including a nucleotide sequence coding for astaxanthin synthase which is involved in the reaction from beta-carotene to astaxanthin in P. rhodozyma, like the AST gene.

In a preferred embodiment, the cloned DNA fragment can be characterized in that
 (a) the nucleotide sequence encodes an enzyme having the amino acid sequence described in SEQ ID NO: 1, or
 (b) the nucleotide sequence encodes a variant of the enzyme selected in (a), which nucleotide sequence is either (i) an allelic variant or (ii) an enzyme having one or more amino acid insertions, deletions, and/or substitutions and having the stated enzyme activity.

In another preferred embodiment, the isolated cDNA fragment can be derived from a gene of Phaffia rhodozyma and is selected from:
 (i) a cDNA sequence represented by SEQ ID NO: 2;
 (ii) an isocoding or an allelic variant for the cDNA sequence represented by SEQ ID NO: 2; and
 (iii) a derivative of a cDNA sequence represented by SEQ ID NO: 2 with insertions, deletions, and/or substitutions of one or more nucleotide(s), and encoding a polypeptide having the enzyme activity.

In another preferred embodiment, the present invention includes the isolated cDNA as described above, which is characterized in that the nucleotide sequence is:
 (i) a nucleotide sequence represented in SEQ ID NO: 2;
 (ii) a nucleotide sequence which, because of the degeneracy of the genetic code, encodes an astaxanthin synthase having the same amino acid sequence as that encoded by the nucleotide sequence in (i); and
 (iii) a nucleotide sequence which hybridizes to the complement of the nucleotide sequence from i) or ii) under standard hybridizing conditions.

In still another preferred embodiment, an isolated genomic DNA fragment can be derived from a gene of *Phaffia rhodozyma* and is selected from:
  (i) a genomic DNA sequence represented by SEQ ID NO: 3;
  (ii) an isocoding or an allelic variant for the genomic DNA sequence represented by SEQ ID NO: 3; and
  (iii) a derivative of a genomic DNA sequence represented by SEQ ID NO: 3 with insertions, deletions, and/or substitutions of one or more nucleotide(s), and coding for a polypeptide having the enzyme activity.

In another preferred embodiment the present invention includes the isolated genomic DNA as described above, which is characterized in that the nucleotide sequence is:
  (i) a nucleotide sequence represented in SEQ ID NO: 3;
  (ii) a nucleotide sequence which, because of the degeneracy of the genetic code, encodes an astaxanthin synthase having the same amino acid sequence as that encoded by the nucleotide sequence in (i); and
  (iii) a nucleotide sequence which hybridizes to the complement of the nucleotide sequence from i) or ii) under standard hybridizing conditions.

Another aspect of the present invention is a recombinant polypeptide having astaxanthin synthase activity and which is involved in the reaction from beta-carotene to astaxanthin in *P. rhodozyma* which is obtainable by the expression of the cloned DNA fragment as set forth above.

A preferred embodiment of the recombinant polypeptide of the present invention is characterized in that
  (a) the polypeptide has an amino acid sequence as described in SEQ ID NO: 1, or
  (b) the polypeptide is a variant of the peptide defined in (a) which is selected from (i) an allelic variant or (ii) an enzyme having one or more amino acid insertions, deletions and/or substitutions and having the stated enzyme activity.

The present invention also includes variants of the polypeptides set forth above. Such variants are defined on the basis of the amino acid sequence of the present invention by insertions, deletions, and/or substitutions of one or more amino acid residues of such sequences wherein such variants still have the same type of enzymatic activity as the corresponding polypeptides of the present invention or they are the result of the well known phenomenon of allelic variation. Such activities can be measured by any assays known in the art or specifically described herein. Such variants can be made either by chemical peptide synthesis known in the art or by recombinant means on the basis of the DNA sequences as disclosed herein by methods known in the state of the art, such as, e.g. that disclosed by Sambrook et al. (Molecular Cloning, Cold Spring Harbour Laboratory Press, New York, USA, second edition 1989).

Amino acid exchanges in proteins and peptides which do not generally alter the activity of such molecules are known in the state of the art and are described, for example, by H. Neurath and R. L . Hill in "The Proteins" (Academic Press, New York, 1979, see especially FIG. 6, page 14). The most commonly occurring exchanges are: Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Art, Asp/Asn, Leu/Ile, Leu/Val, Ala/Glu, Asp/Gly as well as the reverse. It is also possible to add or delete one or several amino acid residues(s) at N- and/or C-terminal of the enzyme without any critical effect on the activity of the present synthase.

Furthermore, the present invention is not only directed to the DNA sequences as disclosed e.g., in the sequence listing as well as their complementary strands, but also to those which include these sequences, DNA sequences which hybridize under standard conditions with such sequences or fragments thereof and DNA sequences, which because of the degeneration of the genetic code, do not hybridize under standard conditions with such sequences but which code for polypeptides having exactly the same amino acid sequence.

The said enzyme activity is expressed as the enzyme activity which renders astaxanthin production to beta-carotene producing microorganism by means of the transformation to express its corresponding gene in the said beta-carotene producing host organisms.

The said enzyme activity is also expressed as the enzyme activity which renders astaxanthin production to microorganism which accumulates intermediate xanthophyll from beta-carotene to astaxanthin described in FIG. 1; e.g. echinenone, beta-cryptoxanthin, canthaxanthin, 3'-hydroxyechinenone, 3-hydroxyechinenone, zeaxanthin, phoenicoxanthin and adonixanthin.

The said enzyme activity can also be expressed as the enzyme activity which catalyzes the astaxanthin formation from various substrates such as beta-carotene, echinenone, beta-cryptoxanthin, canthaxanthin, 3'-hydroxyechinenone, 3-hydroxyechinenone, zeaxanthin, phoenicoxanthin and adonixanthin under appropriate in vitro condition which constitutes of membrane fraction such as natural membrane like microsome and artificial membrane like liposome in company with appropriate electron donor like NADPH."

In the present invention, unless otherwise indicated, the hybridization reactions are generally carried out at 42° C., which is 15 to 35° C. below the $T_m$ of most DNA probes, thus ensuring a maximum rate of hybridization. The desired stringency of hybridization is achieved by washing, e.g., the filter at a salt concentration and temperature that is approximately 5 to 15° C. below the $T_m$ for a perfectly matched hybrid. The salt concentration and temperature, however, may be adjusted to less stringent conditions if significant mismatching of sequence is expected (e.g., when probing for the same gene in a different species or for a different but related sequence).

As used herein, the phrase "standard conditions" for hybridization means the conditions which are generally used by a person skilled in the art to detect specific hybridization signals and which are described, e.g. by Sambrook et al., (s.a.) or preferably so-called stringent hybridization and non-stringent washing conditions, or more preferably so-called stringent hybridization and stringent washing conditions a person skilled in the art is familiar with and which are described, e.g., in Sambrook et al. (s.a) or more preferably so-called medium stringent conditions, e.g. using the DIG (digoxigenin) labeling kit and luminescent detection kit of Boehringer Mannheim (Mannheim, Germany) following the protocol given by the manufacturer and using as the hybridization solution:
  formamide (WAKO, Osaka, Japan) 50% (V/V)
  5×SSC
  blocking reagent (Boehringer) 2% (W/V)
  N-lauroylsarcosine 0.1% (W/V)
  SDS 0.3% (W/V)
at a temperature of 42° C. over night and subsequently washing and detection as indicated by the manufacturer.

For example, a typical wash sequence includes washing the hybridized blot first with a solution A containing 2×SSC/0.1% SDS in water at room temperature. Next, the blot is washed twice in solution B containing 0.1×SSC/0.1% SDS in water at a temperature to be determined based on the desired level of stringency. For example, a perfectly matched hybrid may be washed at a temperature from about 55° to about 65° C.; for a probe from a related gene or from a different species, the wash temperature may be, for example, from about 37° C. to about 52° C. Unless otherwise indicated, this washing condition was used in the present invention.

DNA sequences which are derived from the DNA sequences of the present invention either because they hybridize with such DNA sequences (see above) or can be constructed by the polymerase chain reaction by using primers designed on the basis of such DNA sequences can be prepared either as indicated, namely by the PCR reaction, or by site directed mutagenesis (see e.g., Smith, Ann. Rev. Genet. 19, 423 (1985)) or synthetically as described, e.g., in EP 747 483 or by the usual methods of Molecular Cloning as described, e.g., in Sambrook et al. (s.a.).

The present invention also includes a vector or plasmid that contains a DNA as described above and a host cell transformed or transfected by a DNA as described above or a vector or plasmid as indicated above.

The present invention also provides a recombinant organism which is obtainable by the transformation of a host using a recombinant DNA carrying the DNA as mentioned above.

The present invention also includes a method for producing an enzymatic polypeptide capable of catalyzing the reaction from beta-carotene to astaxanthin, which includes culturing a recombinant organism described above under conditions conductive for the production of the enzymatic polypeptide.

In a further aspect, the present invention provides a method for the production of astaxanthin which includes introducing one or more of the DNAs described above into an appropriate host organism and cultivating this transformed organism under conditions conductive for the production of astaxanthin.

The enzymatic polypeptide of the present invention is also useful in a method for producing astaxanthin, which method includes contacting beta-carotene with a recombinant polypeptide having an astaxanthin synthase activity involved in the reaction from beta-carotene to astaxanthin as set forth above in the presence of an appropriate electron donor in an appropriate reaction mixture containing an appropriate reconstituted membrane. In this method, the recombinant polypeptide may be present in the form of a reconstituted membrane which is prepared from biological membranes such as, for example, microsomes or mitochondrial membranes. The recombinant polypeptide may be also present in the form of a reconstituted artificial membrane, such as for example, a liposome. An electron donor, such as, cytochrome P450 reductase is an example of an appropriate electron donor which can reduce a reaction center of the enzyme of the present invention.

Another embodiment of the invention is an isolated polynucleotide encoding a polypeptide which is SEQ ID NO:1, an isolated polynucleotide which is SEQ ID NO:2, or an isolated polynucleotide which is SEQ ID NO:3.

Another embodiment of the invention is a polypeptide having astaxanthin synthase activity which is SEQ ID NO:1. The present invention also includes a vector containing a polynucleotide which encodes SEQ ID NO:1, a polynucleotide which is SEQ ID NO:2, or a polynucleotide which is SEQ ID NO:3. A host cell is also provided which is transformed with the vector set forth above.

In another embodiment, the present invention provides a process for producing astaxanthin which includes: (a) cultivating in a suitable culture medium a recombinantly produced host cell containing a polynucleotide which encodes a polypeptide having astaxanthin synthase activity.

BRIEF DESCRIPTION OF THE DRAWINGS

The following drawings are included to further illustrate the present invention together with the detailed description given below.

FIG. 1 shows the biosynthetic pathway from acetyl-CoA to astaxanthin in *P. rhodozyma*.

FIG. 2 shows a restriction map of the plasmid pR6 which harbors a partial genomic AST gene.

FIG. 3 shows an expression study for the AST gene to which a 6×His tag was added at its amino terminal end on removal of its transmembrane domain. The cells from 0.1 ml of broth were subjected to 10 % sodium dodecyl sulfide—polyacrylamide gel electrophoresis (SDS-PAGE). Lane 1, Molecular weight marker (105 kDa, 82.0 kDa, 49.0 kDa and 33.3 kDa, up to down, Bio-RAD, Richmond, U.S.A.); Lane 2, *E. coli* (BL21 (DE3) (pLysS) (pAST315) without IPTG); Lane 3, *E. coli* (BL21 (DE3) (pLysS) (pAST315) with 1.5 mM IPTG); Lane 4, molecular weight marker).

DETAILED DESCRIPTION OF THE INVENTION

In general, there are a number of methods to clone a gene encoding biosynthetic enzymes. For example, degenerate PCR can be used. Degenerate PCR is a method to clone a gene of interest which has high homology of its encoded amino acid sequence to that of a known enzyme from other species which have the same or similar function. A degenerate primer, which is used as a set of primers in degenerate PCR, was designed by a reverse translation of the amino acid sequence to corresponding nucleotides ("degenerated"). In such a degenerate primer, a mixed primer which consists of any A, C, G or T, or a primer containing inosine at an ambiguity code is generally used. After cloning of a partial fragment of the gene of interest the genetic fragment containing the entire gene can be screened using the cloned and labeled partial DNA fragment as a probe.

In the case of cloning a gene encoding an enzyme whose activity can be measured by an enzymatic assay, purification of such an enzyme by monitoring enzyme activity and determination of its amino acid sequence for the enzyme is a good method. An amino acid sequence thus obtained is easily translated in reverse into the corresponding nucleotide sequence(s). A DNA fragment which has the corresponding nucleotide sequence can be synthesized iii vitro with a DNA synthesizer and labeled for direct usage as a hybridization probe. An alternative way to obtain a hybridization probe is the degenerate PCR method using the amino acid sequence information.

To clone a gene whose function can not be characterized enzymatically, a method called shot-gun screening has been employed as a conventional cloning method. This method includes the isolation of a mutant strain which lacks the specific gene coding for any of the biosynthetic enzymes of interest, (and transformation of the mutant strain by the DNA prepared from the organism that has an intact gene which corresponds to the gene as such mutated). For an isolation of such a mutant, conventional mutagenesis is often used. Confirmation of the acquired phenotype which is the same as that of the parent strain can be performed by examination of its auxotrophy and the like. In the case that the donor DNA contains the gene which corresponds to the mutated gene in the mutant strain, the transformant by such a gene acquired the same phenotype as the parent strain as a result of genetic complementation.

As a vector, any form of vectors whether they can replicate or not in the cloning host, can be used for shot gun cloning. For the usage of a replicative vector, the capability of complementation is a requisite and it is not necessary that such a vector contain a homologous sequence to the genome of the recipient. In the case of using a non-replicative vector, it is necessary that such a vector contain a homologous sequence to the genome of the host to make a recombination between donor and recipient DNAs.

For cloning of the DNAs of the present invention the method called "color complementation" can be employed. Non carotenogenic organisms, such as *Escherichia coli* can acquire the carotenogenic ability as a result of transformation by carotenogenic genes which could be cloned from carotenogenic organisms such as *Erwinia uredovora*, *Erwinia herbicola* and the like. *E. coli* harboring crtE, crtB, crtI and crtY can produce beta-carotene and color the cells yellow. Exploiting such a characteristic, a number of members of the carotenogenic gene family have been cloned from various carotenogenic organisms such as bacteria and plants. For example, to clone the crtY gene coding for lycopene cyclase, *E. coli* harboring crtE, crtB and crtI on a compatible vector against pUC vector is prepared as a transformation host. Such a host turns red which shows accumulation of lycopene. Next, a cDNA or genomic library from carotenogenic organisms can be constructed using the pUC vector. If the gene corresponding to crtY in the donor carotenogenic organism is present in the transformed plasmid, genetic complementation would occur and the *E. coli* cells would turn yellow which would show the acquisition of the ability to produce beta-carotene. In fact, crtE, crtBY and crtI genes were cloned from *P. rhodozyma* by this method (Verdoes et al., WO 97/23633).

Regarding the cloning of the gene which is involved in the reaction from beta-carotene to astaxanthin, Kajiwara et al. constructed a cDNA expression library from *P. rhodozyma* in the host *E. coli* harboring crtE, crtB, crtI and crtY genes from *E. uredovora* (Kajiwara et al., WO 96/28545, 1996). In such a cloning system, a gene which is involved in the reaction from beta-carotene to astaxanthin could be theoretically cloned from *P. rhodozyma* by judging red pigmentation which shows the accumulation of canthaxanthin or astaxanthin. However, such a gene has not been reported so far. Many researchers speculate about the possibility that membrane-bound carotenogenic enzymes would form an enzyme complex. In such a model, the affinity among carotenogenic enzymes would be necessary for efficient carotenogenesis. Based on such an assumption, this color complementation method is not suitable to clone the enzyme involved in the last step of astaxanthin biosynthesis, namely the one from beta-carotene to astaxanthin, because exogenous enzymes might not have affinity to the Phaffia's carotenogenic enzyme in the sequential reaction of the carotenogenesis.

As used herein, the terms "protein" and "polypeptide" are used interchangeably throughout. The terms "nucleic acid" and "polynucleotide" are likewise used interchangeably.

The term "nucleic acid" is intended to include, without limitation, DNA, RNA, cDNA, and mRNA. As used herein, the DNA may be genomic, synthetic, or semi-synthetic. Moreover, the nucleic acids of the present invention include single-stranded and double stranded molecules.

As used herein "derived from" means that the protein, polypeptide, and/or polynucleotide exists naturally in an organism, such as for example, a *P. rhodozyma*. However, the polypeptides and polynucleotides of the present invention may be produced/obtained from any source. Thus, the present invention includes recombinant, synthetic and semi-synthetic proteins, polypeptides, and polynucleotides.

The compositions of the present invention are said to be "isolated," such as for example "isolated polypeptide," "isolated polynucleotide," etc. As used herein, the term "isolated" is intended to mean that the polypeptide or polynucleotide is purified or, at least partially purified as set forth in more detail in the examples.

In this invention, *P. rhodozyma* ATCC96815 which has been redeposited as a Budapest Treaty deposit at the American Type Culture Collection (ATCC) under accession number 74486 on Feb. 18, 1999 and which is blocked for the reaction from beta-carotene to astaxanthin was used as a transformation host (Schroeder, W. A. and Johnson, E. A., J. Ind. Microbiol. 14, 502–507, 1995). Transformation of this mutant by the genomic library prepared from the chromosome of a wild type strain of *P. rhodozyma* ATCC96594 which has also been redeposited as a Budapest Treaty deposit at the American Type Culture Collection (ATCC) under accession number 74438 on Apr. 8, 1998 was used to isolate a clone which produces astaxanthin. In the present invention, such a genetic fragment complementing the reaction from beta-carotene to astaxanthin in *P. rhodozyma* was isolated and its nucleotide sequence was determined.

Such a gene/DNA of the present invention can be used for overproduction of astaxanthin through a gene dosage effect using gene amplification or promoter modification other than complementation of blocked mutation.

In general, a gene consists of several parts which have different functions. In eukaryotes, genes which encode a corresponding protein are transcribed to premature messenger RNA (pre-mRNA), differing from the genes for ribosomal RNA (rRNA), small nuclear RNA (snRNA) and transfer RNA (tRNA). Although RNA polymerase II (PolII) plays a central role in this transcription event, PolII cannot solely start a transcription without a cis element covering an upstream region containing a promoter and an upstream activation sequence (UAS), and a trans-acting protein factor. At first, a transcription initiation complex which consists of several basic protein components recognizes the promoter sequence in the 5'-adjacent region of the gene to be expressed. In this event, some additional participants are required if the gene is expressed under some specific regulation, such as a heat shock response, or adaptation to a nutrition starvation, and so on. In such a case, a UAS is required to exist in the 5'-untranslated upstream region around the promoter sequence, and certain positive or negative regulator proteins recognize and bind to the UAS. The strength of the binding of the transcription initiation complex to the promoter sequence is affected by such a binding of the trans-acting factor around the promoter, and this enables regulation of the transcription activity.

After activation of a transcription initiation complex by phosphorylation, a transcription initiation complex initiates transcription from the transcription start site. Some parts of the transcription initiation complex are detached as an elongation complex from the promoter region to the 3' direction of the gene (this step is called a "promoter clearance event") and an elongation complex continues transcription until it reaches a termination sequence that is located in the 3'-adjacent downstream region of the gene. Pre-mRNA thus generated is modified in the nucleus by the addition of a cap structure at the cap site which almost corresponds to the transcription start site, and by the addition of polyA stretches at the polyA signal which is located at the 3'-adjacent downstream region. Next, intron structures are removed from the coding region and exon parts are combined to yield an open reading frame whose sequence corresponds to the primary amino acid sequence of the corresponding protein. This modification in which a mature mRNA is generated is necessary for a stable gene expression. cDNA in general terms corresponds to the DNA sequence which is reverse-transcribed from this mature mRNA sequence. It can be synthesized experimentally by a reverse transcriptase derived from certain viral species using a mature mRNA as a template.

In this invention, the mutation point of the *P. rhodozyma* ATCC96815 strain which rendered beta-carotene production to *P. rhodozyma* wild type strain was determined. From the sequencing result, it was suggested that the base change at the splicing sequence of the eighth intron of the AST gene caused such a phenotype as specific beta-carotene accumulation through the improper splicing of mRNA. RT-PCR analysis detected the improper spliced product for the AST gene and strongly supported the identification of the mutation point.

This invention also provides the recombinant AST gene which can be expressed in different host organisms such as *E. coli*. In this invention, a recombinant AST gene was expressed in *E. coli* and it was confirmed that the AST gene's encoded protein product size corresponded to the deduced molecular weight. Biological production of astaxanthin can be realized by using the novel AST gene and such recombinant DNA techniques.

According to the present invention, the gene coding for the enzyme which is involved in the last step of astaxanthin biosynthesis was cloned from a cDNA library of *P. rhodozyma*, and its nucleotide sequence was determined. Furthermore, a part of the genomic DNA including promoter and terminator were cloned and were used to clone the entire gene including the promoter and terminator regions.

An entire gene with its coding region, its intron as well as its regulation regions such as a promoter and terminator were cloned by screening a genomic library, which was constructed in a phage or plasmid vector in an appropriate host using a labeled cDNA fragment as a screening probe. Generally, one of the most common host strains for the construction of a genomic library is *E. coli*. As a vector, a phage vector, such as a lambda phage vector, or a plasmid vector such as a pUC vector can be used. A genomic library constructed in this way, e.g. from *P. rhodozyma* DNA can be screened using a labeled DNA fragment with a portion of the gene of interest as a probe. Hybridized plaques or colonies can then be picked and used for subcloning and/or determination of the nucleotide sequence.

There are several strategies to enhance the desired enzymatic activity of the protein of interest by using its DNA sequence.

One strategy is to use the gene itself in its native form. The simplest approach is to amplify the genomic sequence including its regulatory sequences such as the promoter and the terminator. This can be done by cloning the genomic fragment coding for the enzyme of interest into an appropriate vector with a selectable marker which functions in *P. rhodoyzma*. A drug resistance gene coding for an enzyme that enables the host to survive in the presence of a toxic antibiotic is often used as a selectable marker. The G418 resistance gene harbored in pGB-Ph9 (Wery et al., Gene, 184, 89–97, 1997) is an example of such a vector construction.

As a vector, two types of vectors can be commonly used. One of these types is an integration vector which does not have an autonomous replicating sequence. The plasmid pGB-Ph9 is an example of this type of vector. Because such a vector does not have an autonomous replicating sequence, the above vector cannot replicate by itself and can be present only in an integrated form on the chromosome of the host as a result of a single-crossing recombination using the homologous sequence between a vector and the chromosome. By increasing the concentration of the corresponding drug in the selection medium, the strain in which the integrated gene is amplified on the chromosome can only survive. Another type of vector is a replicable vector which has an autonomous replicating sequence. Such a vector can exist in a multicopy state. In this type of vector, a nutrition complementation maker also can be used in the host which has an appropriate auxotrophy marker. The *P. rhodozyma* ATCC24221 strain which requires cytidine for its growth is one example of such an auxotroph. By using a CTP synthetase as a donor DNA for ATCC2422 1, a host vector system using a nutrition complementation can be established.

Another strategy to overexpress an enzyme of interest is the placement of the gene of interest under a strong promoter. In such a strategy, the gene of interest must not necessarily be in a multicopy state. Furthermore, a promoter whose promoter activity is induced in an appropriate growth phase and an appropriate timing of cultivation can be also used. Production of astaxanthin accelerates in the late phase of growth, such as the production phase of a secondary metabolite. For example, by placing carotenogenic genes under the control of a vegetative promoter, the expression of these genes could be induced in the exponential growth phase and the production of astaxanthin can become tied to the growth of the production strain.

In this invention, the promoter and terminator fragments for the triose phosphate isomerase (TPI) gene was cloned from *P. rhodozyma* as one example of such a constitutive promoter and terminator. Moreover, restoration of astaxanthin production was confirmed in the transformants in which the AST gene was expressed on a different locus (AMY locus on which lies the amylase gene) on the chromosome of beta-carotene producing *P. rhodozyma* ATCC96815 driven by a constitutive promoter and terminator derived from the TPI gene.

Still another strategy to overexpress enzymes of interest is mutation in its regulatory elements. For this purpose, a kind of reporter gene, such as the beta-galactosidase gene, luciferase gene, a gene coding for a green fluorescent protein, and the like is inserted between the promoter and the terminator sequence of the gene of interest so that all the parts including promoter, terminator and the reporter gene are fused and function together. A transformed *P. rhodozyma* in which the reporter gene is introduced on the chromosome or on the vector can be mutagenized in vivo to induce a mutation within the promoter region of the gene of interest. The mutation can be monitored by detecting a change of activity coded for by the reporter gene. If the mutation occurs in a cis element of the gene, the mutation point would be determined by the rescue of the mutagenized gene and sequencing. This mutation can then be introduced to the promoter region on the chromosome by the recombination between the native and the mutated promoter sequence. In the same way, a mutation in the gene which codes for a trans-acting factor can be made.

A mutation can be also induced by in vitro mutagenesis of a cis element in the promoter region. In this approach, a gene cassette, containing a reporter gene which is fused to a promoter region derived from a gene of interest at its 5'-end and a terminator region from a gene of interest at its 3'-end, is mutagenized and then introduced into *P. rhodozyma*. By detecting the difference of the activity of the reporter gene, an effective mutation would be screened. Such a mutation can be introduced in the sequence of the native promoter region on the chromosome by the same method as the case of an in vivo mutation approach.

As donor DNA, a gene coding for an enzyme which catalyzes the reaction from beta-carotene to astaxanthin could be introduced. A coding sequence which is identical to its native sequence, as well as its allelic variant, a sequence which has one or more amino acid insertions, deletions, and/or substitutions as long as its corresponding enzyme has the same type of enzyme activity, can be used. Such a vector can then be introduced into *P. rhodozyma* by transformation and the transformants can be selected by spreading the transformed cells on an appropriate selection medium such as YPD agar medium containing geneticin in the case of pGB-Ph9 or a minimal agar medium omitting cytidine in the case of using auxotroph ATCC24221 as a recipient.

Such a genetically engineered *P. rhodozyma* can be cultivated in an appropriate medium and evaluated for its productivity of astaxanthin. A hyper producer of astaxanthin thus selected would be confirmed in view of the relationship between its productivity and the level of gene or protein expression which is introduced by such a genetic engineering method.

The following examples are provided to further illustrate methods of preparation of the enzyme of the present invention, as well as certain physical properties and uses thereof. These examples are illustrative only and are not intended to limit the scope of the invention in any way.

EXAMPLES

The following materials and methods were employed in the specific Examples described below:

Strains:
- *P. rhodozyma* ATCC96594 (This strain has been redeposited on Apr. 8, 1998 as a Budapest Treaty deposit under accession No. 74438)
- *P. rhodozyma* ATCC96815 (This strain has been redeposited on Feb. 18, 1999 as a Budapest Treaty deposit under accession No.74486)
- *E. coli* DH5alpha F$^-$, phi80d, lacZdeltaM15, delta (lacZYA-argF)U169, hsd (r$_K^-$, m$_K^+$), recA1, endA1, deoR, thi-1, supE44, gyrA96, relA1 (Toyobo, Osaka, Japan)
- *E. coli* XL1-Blue MRF': delta(mcrA)183, delta(mcrCB-hsdSMR-mrr)173, endA1, supE44, thi-1, recA1, gyrA96, relAn1, lac(FproAB, lacI$^q$ZdeltaM15, Tn10 (tet$^r$)) (Stratagene, La Jolla, USA)
- E. coliSOLR: e14$^-$(mcrA), delta(mcrCB-hsdSMR-mrr) 171, sbcC, recB, recJ, umuC::Tn5(kan$^r$), uvrC, lac, gyrA96, relA1, thi-1, endA1, lambda$^R$, (F' proAB, lacI$^q$ZdeltaM15) Su$^-$(nonsuppressing) (Stratagene)
- *E. coli* TOP10:F$^-$, mcrA, delta(mrr-hsdRMS-mcrBC), phi80, delta(lacZ M15), delta(lacX74), recA1, deoR, araD139, (ara-leu)7697, galU, galK, rpsL(Str$^r$), endA1, nupG (Invitrogen, NV Leek, Netherlands)
- *E. coli* BL21 (DE3) (pLysS): dcm$^-$, ompTrB$^-$mB$^-$, lon$^-$ lambda(DE3), pLysS (Stratagene)

Vectors:
- pUC19 (Takara Shuzo, Otsu, Japan)
- lambdaZAPII (Stratagene)
- pCR2.1-TOPO (Invitrogen)
- pET11c (Stratagene)

Media

The *P. rhodozyma* strain is maintained routinely in YPD medium (DIFCO, Detroit, USA). The *E. coli* strain is maintained in LB medium (10 g Bacto-trypton, 5 g yeast extract (DIFCO) and 5 g NaCl per liter). When an agar medium was prepared, 1.5 % of agar (WAKO, Osaka, Japan) was supplemented.

Methods

General molecular biology methods were done according to those described in Molecular Cloning: a Laboratory Manual, 2nd Edition (Cold Spring Harbor Laboratory Press, 1989). Restriction enzymes and T4 DNA ligase were purchased from Takara Shuzo.

Isolation of chromosomal DNA from *P. rhodozyma* was performed using a QIAGEN Genomic Kit (QIAGEN, Hilden, Germany) following the protocol supplied by the manufacturer. A mini-prep of plasmid DNA from transformed *E. coli* was performed with the Automatic DNA isolation system (PI-50, Kurabo, Co. Ltd., Osaka, Japan). A midi-prep of plasmid DNA from an *E. coli* transformant was performed using a QIAGEN column (QIAGEN). A DNA fragment was isolated and purified from agarose using QIAquick or QIAEX II (QIAGEN).

Fluorescent DNA primers for DNA sequencing were purchased from Pharmacia. DNA sequencing was performed with the automated fluorescent DNA sequencer (ALFred, Pharmacia, Uppsala, Sweden).

Competent cells of DH5alpha were purchased from Toyobo.

The apparatus and reagent for biolistic transformation of *P. rhodozyma* were purchased from Nippon Bio-Rad Laboratories (Tokyo, Japan).

Example 1

Isolation of Genomic DNA from *P. rhodozyma*

To isolate a genomic DNA from *P. rhodozyma*, ATCC96594 the QIAGEN genomic kit was used according to the method specified by the manufacturer.

At first, cells of *P. rhodozyma* ATCC96594 from 100 ml of overnight culture in YPD medium were harvested by centrifugation (1500×g for 10 min.) and washed once with TE buffer (10 mM Tris/HCl (pH 8.0) containing 1 mM EDTA). After suspending in 8 ml of Y1 buffer of the QIAGEN genomic kit, lyticase (SIGMA, St. Louis, USA) was added at a concentration of 2 mg/ml to disrupt the cells by enzymatic degradation. The reaction mixture was incubated for 90 minutes at 30° C. and then proceeded to the next extraction step. Finally, 20 μg of genomic DNA was obtained.

Example 2

Construction of a Genomic Library from *P. rhodozyma* ATCC 96594

As described in the section "detailed description of the invention", a plasmid harboring a drug resistant marker cassette was constructed by inserting a G418 resistant structure gene between the promoter and terminator region of the gene of the glyceraldehyde-3-phosphate dehydrogenase (GAP) and ligating this cassette into the KpnI- and HindIII-digested pUC19. This plasmid was named pUC-G418 and used further on. Then, a ClaI linker was ligated into the unique EcoRI site of the pUC-G418 vector and the resultant plasmid pUC-G418C1512 was obtained and used as a vector backbone in the construction of the Phaffia's genomic library.

Then, 10 μg of chromosomal DNA prepared from *P. rhodozyma* ATCC96594 as described above in Example 1 was digested partially with 1.6 units of HpaII for 45 minutes at 37° C. and was subjected to agarose gel electrophoresis. After staining by ethidium bromide, partially digested DNA species (i.e., fragments) from 4 to 10 kb were recovered by electroelution using a dialysis membrane. After ethanol precipitation of recovered HpaII fragments, 1.215 μg of DNA was obtained. Next, 3 μg of pG418C1512 was digested by 10 units of ClaI for an hour at 37° C. and precipitated with ethanol. ClaI-digested pG418C1512 was then dephosphorylated using calf intestine alkaline phosphatase. ClaI-digested and dephosphorylated pG418C1512 vector was then subjected to agarose gel electrophoresis and the DNA fragment was recovered using the QIAquick protocol according to the instructions of the manufacturer. Finally, 2.62 pg of ClaI-digested and dephosphorylated pG418C1512 was obtained.

2.62 μg of ClaI-digested and dephosphorylated pG418C1512 was ligated to 1.22 μg of HpaII-partially digested Phaffia's genomic DNA over night at 16° C. and the resultant ligation solution was used as donor DNA for the transformation of an *E. coli* DH5alpha strain. The total ligation mixture (270 μl) was transferred to 1 ml of competent cells of DH5alpha (Toyobo). After a heat shock treatment at 42° C. for 45 seconds succeeded by maintenance on ice for 30 minutes, the transformed cells were placed on ice for 2 minutes and then incubated at 37° C. for an hour with the addition of 5 ml of SOC medium containing:

0.5% yeast extract (DIFCO)

2% trypton (DIFCO)

10 mM NaCl 2.5 mM KCl 10 mM $MgCl_2$ 20 mM $MgSO_4$ 20 mM glucose.

The incubated cells were transferred into 100 ml of LB medium containing 100 microgram/ml of ampicillin. Cultivation was continued overnight at 37° C. and then the cells were harvested for plasmid midi-preparation.

A plasmid library was prepared from harvested cells using QIAGEN midi-prep columns according to the method supplied by the manufacturer. Finally, 0.3 mg/ml of Phaffia's genomic library was obtained in a total volume of 5 ml and used as a genomic library.

Example 3

Transformation of *P. rhodozyma* ATCC96815 with a Biolistic Method

Transformation was done according to the method described in Methods in Molecular Biology (Johnston et al., 53; 147–153, 1996). As a host strain, *P. rodozyma* ATCC96815 was cultured in YPD medium to the stationary phase. After centrifugation of the broth, cells were concentrated 10-fold with sterilized water and 200 μl of the cell suspension was spread on YPD medium containing 100 microgram/ml of geneticin, and 0.75 M of mannitol and sorbitol. Five micrograms of a genomic library, prepared as described in Example 2, was coated on 1.5 mg of 0.9 μm gold particle, and used as donor DNA for the biolistic transformation. Approximately 20,000 geneticin-resistant clones were yielded (300 to 500 colonies per plate) after one week of incubation at 20° C. Although most of the transformants showed a yellow color (as the host strain, ATCC96815 did), three colonies pigmented red and were used further on.

Example 4

Analysis of Carotenoid Obtained From Red-pigmented Transformants

Red-pigmented transformants obtained from *P. rhodozyma* ATCC96815 (Example 3) were cultivated in 10 ml of YPD medium at 20° C. in test tubes. Then, cells were harvested from 0.5 ml of broth and used for the extraction of carotenoids from cells. The carotenoid content of *P. rhodozyma* was measured by HPLC after extraction of the carotenoids from cells of *P. rhodozyma* by disruption with glass beads as described. After extraction, disrupted cells were then collected by centrifugation and the resultant supernatant was analyzed for carotenoid content by HPLC.

HPLC column; Chrompack Lichrosorb si-60 (4.6 mm, 250 mm)

Temperature; room temperature

Eluent; acetone/hexane (18/82) add 1 ml/L of water to elluent

Injection volume; 10 μl

Flow Rate; 2.0 ml/minute

Detection; UV at 450 nm

A sample of beta-carotene was purchased from SIGMA and astaxanthin was obtained from Hoffman La-Roche (Basel, Switzerland).

As a result of HPLC analysis, it was confirmed that all three red transformants produced astaxanthin specifically though the host strain, ATCC96815 produced only beta-carotene.

Example 5

Plasmid Rescue From the Chromosome of Red Transformants (of Example 3) Which Produced Astaxanthin Chromosomal DNA was prepared from all the astaxanthin-producing transformants. For this purpose, the QIAGEN genomic kit was used according to the method specified by the manufacturer, as described in Example 1. 5 μg of chromosomal DNA, thus prepared, was digested by HindIII and then purified according the QIAquick protocol. *E. coli* DH5alpha competent cells were transformed by the ligated DNA solutions and then spread on LB agar medium containing 100 μg/ml of ampicillin. All of the transformants had the same insert fragments in their plasmids, judging from sequence analysis of the plasmids. This indicated that three independent red transformants derived from *P. rhodozyma* ATCC96815 were yielded by the same type of recombination event between the donor DNA of the genomic library and chromosomal DNA. One of the plasmids thus rescued was named pR2-4 and used further on.

Example 6

Screening of the Original Genomic Library By Using pR2-4 as a Hybridization Probe Because the rescued fragment in pR2-4 may have mutations depending on the direction of the recombination event yielding red transformants of *P. rhodozyma*, screening of the original genomic library was done by using pR2-4 as a hybridization probe.

For this purpose, twenty thousand *E. coli* transformants of the original genomic library, as described in Example 2 were transferred to nylon membrane filters (Hybond-N+, Amersham, Buckinghamshire, UK) and subjected to colony hybridization. Three transformants which harbored the same nucleotide sequence in their insert as that of pR2-4 were isolated. The isolated plasmids from these transformants were named pR3, pR5.1 and pR16.

Next, *P. rhodozyma* ATCC96815 was transformed by pR3, pR5.1 and pR16. All the transformants colored red. This result suggests that the isolated plasmids might contain the gene encoding an enzyme involved in the reaction of beta-carotene to astaxanthin in *P. rhodozyma*. We designated this gene as AST gene. Among these plasmids, pR16 was used further on.

Example 7

Isolation of mRNA From *P. rhodozyma* for cDNA Analysis

To analyze the pattern of transcripts from *P. rhodozyma*, total RNA was isolated from *P. rhodozyma* ATCC96594 and ATCC96815 by phenol extraction by combination of the cell disruption with glass beads and purified mRNA using an mRNA separation kit (Clontech, Palo Alto, USA).

At first, cells of ATCC96594 and ATCC96815 strains from 10 ml of a two-day-culture in YPD medium were harvested by centrifugation (1500×g for 10 min.) and washed once with extraction buffer (100 mM Tris/HCl (pH 7.5) containing 0.1 M LiCl and 0.1 mM EDTA). After filling up to 5.0 ml of cell suspension with the same extraction buffer in 50 ml disposable centrifuge tube (IWAKI Glass, Tokyo, Japan), 1.5 ml of isogen-LS (Nippon gene, Toyama, Japan) and 10 grams of glass beads were added. Centrifuge tubes which contained the cell suspension with isogen-LS and glass beads were shaken with a horizontal table top shaker for an hour. In this step, 300 $\mu$g of total RNA was recovered.

Then, mRNA was purified using an mRNA separation kit (Clontech). On 8.0 $\mu$g of mRNA from *P. rhodozyma* ATCC96594 and ATCC96815 strains were obtained.

To synthesize cDNA, we used the SMART cDNA construction kit (Clontech) according to the method specified by the manufacturer. We applied 2 $\mu$g of purified mRNA for a first strand synthesis followed by PCR amplification and obtained 1 mg of cDNA.

Example 8

Subcloning of pR16 and Functional Analysis of its Insert Fragment

The restriction map of pR16 is depicted in FIG. 12. Each EcoRI fragment whose length was 0.7 and 2.7 kb, was subcloned into pUC-G418 and named pRS913 and pRLR913, respectively.

Then, the astaxanthin-producing *P. rhodozyma* ATCC96594 strain was transformed with pRS913. As a result of this transformation study, yellow transformants were yielded. This suggested that 0.7 kb EcoRI fragment might contain a truncated AST gene and the transformation via a single-cross recombination between a 0.7 kb EcoRI fragment and its homologous sequence on the choromosome of *P. rhodozyma* would result in a gene disruption of the AST gene on the choromosome of *P. rhodozyma*.

Next, the beta-carotene-producing ATCC96815 strain was transformed with pRLR913 and red transformants were yielded. This suggested that the mutation point of strain ATCC96815 which led the astaxanthin-producing wild type strain to produce beta-carotene would lie in the 2.7 kb EcoRI fragment originally adjacent to the 0.7 kb EcoRI fragment in pR16.

Two hundred $\mu$g of cDNA prepared in Example 7 was subjected to agarose gel electrophoresis for virtual Northern analysis. In the case of the cDNAs prepared from ATCC96594 and 96815, two bands which, namely at 3.2 and 2.0 kb were hybridized in both cases by using the 2.7 kb EcoRI fragment of pRLR913 as a hybridization probe. This suggested that the ast mutation of ATCC96815 would be a point mutation which did not reflect a change in the length of mRNA such as a missense mutation.

In the case of using the 0.7 kb EcoRI fragment of pRS913 as a hybridization probe, a band of 2.0 kb was hybridized. From this study, it seemed that the AST gene might give a 2.0 kb transcript in *P. rhodozyma*.

Example 9

Cloning of the cDNA of the ast Gene

To clone the cDNA for the AST gene from *P. rhodozyma*, we constructed cDNA library from *P. rhodozyma* ATCC96594. Total RNA was isolated by phenol extraction by combination of the cell disruption with glass beads as described in Example 7.

At first, cells of the ATCC96594 strain from 50 ml of a two-day-culture in YPD medium were harvested by centrifugation (1500×g for 10 min.) and washed once with extraction buffer (100 mM Tris/HCl (pH 7.5) containing 0.1 LiCl and 0.1 mM EDTA). After filling up to 5.0 ml of cell suspension with the same extraction buffer in 50 ml disposable centrifuge tubes (IWAKI Glass), 1.5 ml of isogen-LS (Nippon gene) and 10 grams of glass beads were added. Centrifuge tubes which contained cell suspension with isogen-LS and glass beads were shaken with a horizontal table top shaker for an hour. In this step, 1.8 mg of total RNA was recovered.

Then, mRNA was purified using the PolyATtract mRNA isolation system (Promega corp., Madison, USA) according to the method specified by the manufacturer. Finally, we obtained 8.0 $\mu$g of mRNA from the *P. rhodozyma* ATCC96594 strain.

To construct a cDNA library, 8.0 $\mu$g of the purified mRNA was used in the COPY kit (Invitrogen, Carlsbad, USA) with the protocol specified by the manufacturer. After ligation of an EcoRI adaptor (Stratagene), synthesized cDNA was subjected to agarose gel electrophoresis. After the excision of the agarose gel piece which covered the length of cDNAs from 1.9 to 2.3 kb, the collected cDNA species were purified by QIAEX II (QIAGEN). This size-fractionated cDNA was ligated to EcoRI-digested and dephosphorylated lambdaZA-PII (Stratagene). The over-night ligation mixture was in vitro packaged with Gigapack III gold extract (Stratagene) and used to infect an *E. coli* XL1-Blue MRF' strain.

Conventional plaque screening was performed against 6000 plaques using 2.7 and 0.7 kb EcoRI fragment as described in Example 8 as hybridization probes. One plaque hybridized strongly to these probes, and was picked up with a sterilized toothpick and the eluted phage particle were used for in? vivo excision, according to the method specified by the manufacturer. Finally, infected transformants of *E. coli* SOLR cells which showed resistance against ampicillin were isolated. After sequencing of the isolated plasmids obtained from these transformants, it turned out that these plasmids contained the same fragment as a part of the sequence of pR6 which was described in Example 6.

The entire sequence of the cDNA of the AST gene was determined and is shown as SEQ ID NO: 2 and its deduced amino acid sequence as SEQ ID NO: 1.

Example 10

Expression of AST Gene in *E. coli*

To confirm that the ORF for the AST gene actually encodes a protein, an expression study of the AST gene was performed in an *E. coli* expression system. At first, a 6×histidine (His) tag was added to the carboxyl terminal end of the AST product in order to make it easy to purify. PCR primers whose sequences are listed in TABLE 1 were synthesized.

Table 1

PCR primers for cloning 3' portion of AST gene to which a 6×His tag is added
ast13:
GTTCAAAGTTCATTTATGGA (sense primer) (SEQ ID NO: 4)
ast14:
GGATCCTCAGTGGTGGTGGTGGTGGTGT-TCGACCGGCTTGACCTGCA (antisense primer) (SEQ ID NO: 5)

Next, 1.5 kb of NdeI/EcoRI fragment of pAST1207 and 0.3 kb of EcoRI/BamHI fragment of pAST 114 were ligated into pET11c which was digested by NdeI and BamHI and ligated DNA was transformed into *E. coli* JM109 strain. Six independent ampicillin resistant clones were examined by restriction analysis and it was found that 5 of 6 clones had the correct structure of the recombinant expression plasmid containing AST gene. One of these clones was selected for further study (pAST 120) and then transformed into *E. coli* BL21 (DE3) (pLysS) strain. It was revealed that all of the ampicillin resistant clones which were examined by restriction analysis possessed pAST 120 properly.

Next, an expression study was performed by addition of 1 mM IPTG to *E. coli* BL21 (DE3) (pLysS) (pAST120) growing culture when the optical density (OD) at 600 nm reached 0.8. After continuation of cultivation at 37° C. for 4 hours, cells were harvested by centrifugation and lysed by boiling in SDS sample buffer (125 mM Tris-HCl, pH 6.8, 20% glycerol, 4% SDS, 0.005% bromophenol blue, 5% mercaptoethanol). The lysate was then subjected to SDS-polyacrylamide gel electrophoresis (PAGE). Expressed protein was not observed after staining by coomassie brilliant blue (Rapid stain CBB kit, nacalai tesque, Kyoto, JAPAN) (data not shown).

In general, it is reported that some modifications of amino acid sequence at the amino terminal region of the P450 protein is required to express P450 protein in an *E. coli* expression system. In fact, the AST gene which had an intact sequence was not expressed in *E. coli* (data not shown) and it was found that some modifications the amino terminal sequence was necessary in the case of the AST gene as well as other P450 enzymes. As a next strategy for expression of a recombinant AST gene, the construction, in which 6×His tag sequence was added at the amino terminal end of the AST protein on the deletion of the hydrophobic anchor sequences which were located at the amino terminal end of the AST gene, was made.

In order to add a 6×His tag sequence at the amino terminal end of the AST protein, anchor sequences were deleted at the amino terminal end, and the following PCR primers were synthesized (Table 2) and used for PCR cloning.

Table 2

PCR primers for cloning the AST gene lacking an anchor sequence at its 5' portion to which 6×His tag is added
ast32:
CATATGCACCACCACCACCACCACCTG-TATAACCTTCAGGGGCCC (sense primer for cloning of 5' end of AST gene) (SEQ ID NO: 6)
ast2:
GTAACAACACCATCTCCGGT (antisense primer for cloning of 5' end of AST gene) (SEQ ID NO: 7)
ast13:
GTTCAAAGTTCATTTATGGA (sense primer for cloning of 3' end of AST gene) (SEQ ID NO: 4)
ast33:
GGATCCTCAACTCATTCGACCGGCTT (antisense primer for cloning of 3' end of AST gene) (SEQ ID NO: 8)

The PCR conditions were as follows: 25 cycles of 15 seconds at 94° C., 30 seconds at 55° C. and 30 seconds at 72° C. The plasmid, pAST1207 was used as PCR template. PCR fragments which had the desired length were cloned into pCR2.1-TOPO (Invitrogen) and 6 independent clones which had expected inserts were examined for their insert sequence. As a result, two of the clones had the exact insert sequence, and one clone was selected and used for further study (pAST228 for 3' end of AST gene and pAST302#3202 for 5' end of AST gene, respectively). A 0.2 kb NdeI/SphI fragment from pAST302#3202, 1.5 kb SphI/EcoRI fragment from pAST1207 and 0.05 kb KpnI/BamHI fragment from pAST228 were ligated into pET11c digested by NdeI and BamHI and the ligated mixture was transformed into *E. coli* DH5alpha.

As a result of restriction analysis for 6 independent clones, it was found that all the clones had the correct structure harboring the AST gene for its expression. One clone was selected and used for further study (pAST315). Next, pAST315 was transferred into expression host *E. coli* BL21 (DE3) (pLysS). It was confirmed that all the 6 transformants had pAST315 correctly as a result of restriction analysis.

Next, an expression study was performed by addition of 1.5 mM IPTG to *E. coli* BL21 (DE3) (pLysS) (pAST315) growing culture when the optical density (OD) at 600 nm reached 0.93. After continuation of cultivation at 37° C. for 4 hours, cells were harvested by centrifugation and lysed by boiling in SDS sample buffer. The lysate was then subjected to PAGE. An expressed protein whose molecular weight corresponded well with its deduced amino acid sequence (approximate 60 kDa) was observed after staining by coomassie brilliant blue (FIG. 13). From this result, it was confirmed that the AST gene encodes a protein expected from its deduced open reading frame.

Example 11

In Vitro Characterization of the AST Gene Product

For the enzymatic characterization of the AST gene product, a standard assay which is used for the characterization of P450 enzymes can be applied. For this purpose, it is necessary that the reaction mixture contains a reconstituted membrane. As a reconstituted membrane, natural isolates such as mitochondrial membranes or microsomes and artificial membranes are often used. It is necessary that an electron transfer between an electron acceptor and a receptor can occur. As an electron donor, cytochrome P450 reductase is often added to the reaction mixture. As an electron acceptor, oxygen molecules are involved. Under the presence of an electron source, such as reduced NADPH+, beta-carotene, which is a substrate of astaxanthin synthase can be converted to astaxanthin. Produced astaxanthin can be assayed qualitatively and quantitatively with HPLC analysis.

Example 12

Cloning of a Genomic Fragment Containing the AST Gene

To determine the genomic sequence containing the AST gene, a sequencing experiment was performed using a primer-walking procedure. Sequencing analysis of pRS913 showed that pRS913 did not contain the 3' end of the AST gene. To obtain the 3'-adjacent genomic fragment to the AST gene, a genome-walking experiment was performed. To do this, a universal genome walker kit (Clontech) was exploited according to the method specified by the manufacturer. As a template of PCR, chromosomal DNA prepared in Example 1 was used. A gene specific primer, ast15 whose sequence was as listed in TABLE 3 was synthesized and used as a PCR primer.

Table 3

Sequence of primer used for genome walking of the AST gene
ast15:
TAGAGAGAAGGAGGGGTACCAGATGC (SEQ ID NO. 9)

PCR fragments an which had appropriate length (smaller than 1 kb) were obtained from an EcoRV and StuI library, purified and cloned into pCR2.1-TOPO (Invitrogen). As a result of sequencing, it was found that both fragments contained the genomic fragment encoding the AST gene. Based on the sequence which was located at 200 bp from the polyA site for the AST gene, PCR primer was designed as listed in TABLE 4.

Table 4

Sequence of primer for cloning of 3'-adjacent fragment to the AST gene
ast18:
CCCCGGATTGTGGAGAAACT (SEQ ID NO: 10)

By using ast15 and ast18 primers as PCR primers and chromosomal DNA prepared in Example 1 as PCR template, PCR was conducted. Proof-reading polymerase (HF polymerase, Clontech) ensured the amplification of a PCR fragment which had the exact sequence. PCR condition was as follows; 25 cycles of 15 seconds at 94° C., 30 seconds at 55° C. and 30 seconds at 72° C. Six independent clones which had 400 bp inserts showed the identical sequence.

By combining the sequences from pRS913 and pRL913, a 3.9 kb sequence containing the AST gene having a 474 bp promoter region and a 269 bp terminator region was determined (SEQ ID NO. 3). As a result, the AST gene showed intron-rich structure (17 introns).

Example 13
Determination of Mutation Point in Beta-carotene Producing Strain, P. rhodozyma ATCC96815

To confirm the fact that beta-carotene production by the P. rhodozyma ATCC96815 strain was caused from the mutation within the AST gene, a genomic sequence containing the AST gene obtained from ATCC96815 and its parent strain P. rhodozyma ATCC24230 were determined. To do this, PCR primers whose sequences were as listed in TABLE 5 were synthesized and used for PCR cloning.

Table 5

PCR Primers for Cloning the Entire Genomic ast Gene;
ast21:
ATGTTCATCTTGGTCTTGCT (sense primer) (SEQ ID NO: 11)
ast4:
ACGTAGAAGTCATAGCGCCT (antisense primer) (SEQ ID NO: 12)

By using HF polymerase (Clontech) as PCR polymerase and chromosomal DNA prepared from strains, ATCC96815 and ATCC24230 by the same protocol as Example 1 as PCR template, PCR was performed under the condition as follows; 25 cycles of 15 seconds at 94° C., 30 seconds at 55° C. and 4 minutes at 72° C. PCR fragments obtained whose length were approximately 3.5 kb were cloned into pCR2.1-TOPO and sequenced for their entire sequences by the primer walking procedure. Between the sequence for P. rhodozyma ATCC96594 strain and ATCC24230 strain, 7 base changes were found. Four base changes were found in its exon sequence but those did not give any amino acid changes. Three base changes were found in its intron structure. In comparison between beta-carotene producing strain ATCC96815 and its parent strain, ATCC24230, one base change which was located at the 5'-splicing sequence (GTAAGT>GTAAAT) within the eighth intron was found. This might indicate that the mutation which conferred the phenotype of beta-carotene accumulation on astaxanthin-producing P. rhodozyma was caused by improper splicing of the mRNA for the AST gene.

To confirm this assumption, RT-PCR was performed using cDNA prepared from P. rhodozyma ATCC96815 as PCR template. mRNA was isolated from P. rhodozyma ATCC96815 by the same protocol as Example 9 and used for the synthesis of cDNA. To obtain cDNA from this mRNA prepared from ATCC96815 by the PCR method, a SMART PCR cDNA library construction kit (Clontech) was exploited according to the method specified by supplier. The following primers whose sequence are as listed in TABLE 6 and which covered the eighth intron were synthesized and used for PCR primers.

Table 6

PCR primers for RT-PCR to detect the improper splicing product for the AST gene
ast7:
TTTGACTCAAGGATTAGCAG (sense primer) (SEQ ID NO: 13)
ast26:
TGTCTTCTGAGAGTCGGTGA (antisense primer) (SEQ ID NO: 14)

RT-PCR conditions were as follows: 25 cycles of 15 seconds at 94° C., 30 seconds at 55° C. and 30 seconds at 72° C. As a result of PCR, 300 bp of PCR products were amplified and cloned into pCR2.1-TOPO. Two independent clones which had 300 bp inserts were sequenced. As a result, it was confirmed that improper splicing products for the AST gene were synthesized in the P. rhodozyma ATCC96815 strain. Improper splicing in the eighth intron of the AST gene might cause the production of shorter truncated AST proteins than the AST protein spliced properly because a stop codon lies in the eighth intron. This result indicated that the mutation point lies in the AST gene which failed in the proper splicing.

Example 14

Expression of the AST Gene in a Beta-carotene-producing *Phaffia rhodozyma*

To confirm that the AST gene encoded the enzyme which was involved in the conversion of beta-carotene to astaxanthin, the AST gene was cloned into a beta-carotene-producing strain. To exclude the possibility of recombination at a native locus of the AST gene on the chromosome, an expression plasmid for the AST gene on the AMY locus of *Phaffia rhodozyma*'s chromosome was constructed. To do this, cloning of some genetic elements from *Phaffia rhodozyma* was required.

1) Cloning of the Constitutive Promoter and Terminator from *Phaffia rhodozyma*

To clone a constitutive promoter and terminator from *Phaffia rhodozyma*, a degenerate PCR method was exploited. Among the genes which are often used as a constitutive promoter and terminator in yeast genetics, the TPI gene which encode triose phosphate isomerase was cloned. Among the conserved amino acid sequence registered in Blocks database (http://www.blocks.fhcrc.org/), two motif sequences (Arg-Thr-Phe -Phe-Val-Gly-Gly-Asn and Asp-Val-Asp-Gly-Phe-Leu-Val-Gly-Gly-Ala) were selected and their degenerate primers were synthesized as follows.

Table 7

Degenerate PCR primers for cloning of the TPI gene from *P. rhodozyma* tp1:
MGNACNTTYTTYGTNGGNGGNAAY (sense primer) (SEQ ID NO: 15)

tp6:
GCNCCNCCNACNARRAANCCRTCNACRTC (antisense primer) (SEQ ID NO: 16)

(M=A or C; N=A, C, G or T; Y=C or T; R=A or G)

PCR conditions were as follows: 25 cycles of 15 seconds at 94° C., 30 seconds at 46° C. and 15 seconds at 72° C. ExTaq polymerase (Takara Shuzo) was used as the PCR polymerase. As a PCR template, a cDNA pool was prepared from mRNA isolated from *P. rhodozyma* ATCC96594 using a SMART PCR cDNA library construction kit (Clontech). A 0.7 kb PCR fragment was purified and cloned into pCR2.1-TOPO. Six independent clones had inserts having the desired length, judging from restriction analysis. Two of these clones were sequenced and it was confirmed that both of them had an insert sequence which had striking homology to known TPI genes from various organisms. One of these clones was selected for further study (pTPI923).

Next, based on the insert sequence of pTPI923, several PCR primers whose sequences are listed in TABLE 8 were synthesized for genome walking to clone the promoter and terminator of the TPI gene. For this experiment, an universal genome walker kit (Clontech) was exploited according to the method specified by the manufacturer.

Table 8

PCR primers for genome walking to clone the TPI promoter and terminator
tp9:
GCTTACCTCGCTTCCAACGTTTCCCAG (terminator cloning, primary) (SEQ ID NO: 17)
tp10:
GGATCTGTCTCTGCCTCCAACTGCAAG (terminator cloning, nested) (SEQ ID NO: 18)
tp11:
GGGTCAATGTCGGCAGCGAGAAGCCCA (promoter cloning, primary) (SEQ ID NO: 19)
tp12:
ATGTACTCGGTAGCACTGATCAAGTAG (promoter cloning, nested) (SEQ ID NO: 20)

PCR conditions were as follows: 7 cycles of 4 seconds at 94° C. and 3 minutes at 74° C., followed by 32 cycles of 4 seconds at 94° C. and 3 minutes at 69° C. and succeeded to extension at 69° C. for 4 minutes. KOD polymerase (TOYOBO) was used as the PCR polymerase. Chromosomal DNA prepared from *P. rhodozyma* ATCC96594 was used as a PCR template. As a result, candidate for the terminator region was obtained from the EcoRV and StuI library. Sequencing analysis for these candidates revealed that both clones had the downstream sequence for the TPI gene containing the deduced 3' end of the TPI structural gene and terminator region. In case of cloning for the promoter region' candidates which were obtained from the EcoRV library contained the deduced 5' end of the TPI structural gene and promoter region.

Then, PCR primers whose sequences are listed in TABLE 9 were synthesized for the construction of promoter cassette and terminator cassette derived from TPI gene.

Table 9

PCR primers to construct the TPI promoter and the TPI terminator cassette
tp13:
GCGGCCGCATCCGTCTCGCCATCAGTCT (sense primer for promoter cassette) (SEQ ID NO: 21)
tp14:
CCTGCAGGTCTAGAGATGAATAAATATAAAGAGT (antisense primer for promoter cassette) (SEQ ID NO: 22)
tp15:
CCTGCAGGTAAATATATCCAGGGATTAACCCCTA (sense primer for terminator cassette) (SEQ ID NO: 23)
tp16:
GGTACCCGTGCGCAGTCGACCGAGACAT (antisense primer for terminator cassette) (SEQ ID NO: 24)

PCR condition were as follows: 25 cycles of 15 seconds at 94° C., 30 seconds at 55° C. and 30 seconds at 72° C. HF polymerase (Clontech) was used as the PCR polymerase and yielded PCR fragments which were cloned into pCR2.1-TOPO. As a result of restriction and sequencing analysis, it was found that clones which had identical sequences were obtained. Each clone was selected for further study (pTPIP1104 for promoter cassette and pTPIT1104 for terminator cassette, respectively).

2) Cloning of Partial Amylase Gene from Phaffia rhodozyma

To locate and express a foreign gene on the chromosome of *P. rhodozyma*, the amylase gene was cloned from *P. rhodozyma*. In case that expression vector on which the foreign gene would be cloned could contain an homologous genetic fragment to the chromosomal sequence of *P. rhodozyma*, such as an amylase gene, an expression vector can be integrated on the homologous region on the chromosome of *P. rhodozyma* after the single cross recombination.

Eleven amino acid sequences encoding amylase from various organisms were selected from the Entrez database (http://www.ncbi.nlm.nih.gov/Entrez/) and used for amino acid alignment by clustal W (Thompson, J. D., Higgins, D. G. and Gibson, T. J., Nucleic Acids Research, 22: 4673–4680, 1994). The eleven organisms whose amylase sequences were registered on the database are as listed in TABLE 10.

Table 10

Various amylase genes which were registered on the database for clustal W analysis

*Aspergillus niger* var. awamori amyA gene (accession number X52755)
*Aspergillus niger* var. awamori amyB gene (accession number X52756)
*Aspergillus kawachii* acid-stable alpha-amylase gene (accession number AB008370)
*Aspergillus oryzae* amyl gene (accession number X12725)
*Aspergillus shirousamii* alpha-amylase gene (accession number P30292)
*Cryptococcus* species alpha-amylase gene (accession number D83541)
*Lipomyces kononenkoae* subsp. spencermartinsiae alpha-amylase gene (accession number U30376)
*Debaryomyces occidentalis* amy1 gene (accession number X 16040)
*Saccharomycopsis fibuligera* ALP1 gene (accession number X05791)
*Schizosaccharomyces pombe* alpha-amylase gene (accession number Z64354)

Two conserved amino acid sequences (Asp-Tyr-Ile-Gln-Gly-Met-Gly-Phe -Asp/Thr-Ala-Ile-Trp and Asp-Gly-Ile-Pro-Ile-Ile-Tyr-Tyr-Gly-Thr-Glu-Gln) for amylase were selected to clone the amylase gene from *P. rhodozyma* by a degenerate PCR method. Then, PCR primers whose sequences are listed in TABLE 11 were synthesized for the cloning of the AMY gene from *P. rhodozyma*.

Table 11

Degenerate PCR primers for cloning of amylase (AMY) gene from *P. rhodozyma*
amy1:
GAYTAYATHCARGGNATGGGNTTYRMNGCNATHTG (sense primer) (SEQ ID NO: 25)
amy2:
TGYTCNGTNCCRTARTADATDATNGGDATNCCRTC (antisense primer) (SEQ ID NO: 26)
(Y=C or T; H=A, C or T; R=A or G; N=A, C, G or T; M=A or C; D=A, G or T)

PCR conditions were as follows: 25 cycles of 15 seconds at 94° C., 30 seconds at 50° C. and 2 minutes at 72° C. ExTaq polymerase (Takara Shuzo) was used as PCR polymerase. As a PCR template, chromosomal DNA prepared in Example 1 and the cDNA pool prepared from mRNA isolated from *P. rhodozyma* ATCC96594 using the SMART PCR cDNA library construction kit (Clontech) were used. 1.7 kb and 0.9 kb PCR fragments were yielded when chromosome and cDNA were used as PCR template, respectively. Both fragments were purified and cloned into pCR2.1-TOPO. Six independent clones had inserts having the desired length, judging from restriction analysis. Two of these clones were sequenced and it was confirmed that both of them had insert sequence which had striking homology to known amylase genes from various organisms. One of these clones which contained a chromosomal AMY fragment was selected for further study (pAMY216). To construct a partial amylase cassette, two PCR primers whose sequences are listed in TABLE 12 were synthesized based on the internal sequence of the insert fragment of pAMY216.

Table 12

PCR primers to construct a partial AMY cassette
amy101:
CCGCGGCATTGATACCTCTACCCCGT (sense primer for AMY cassette) (SEQ ID NO:27)
amy102:
GCGGCCGCCTGCAATCCTGGATCCACCG (antisense primer for AMY cassette) (SEQ ID NO: 28)

PCR conditions were as follows: 25 cycles of 15 seconds at 94° C., 30 seconds at 55° C. and 2 minutes at 72° C. HF polymerase (Clontech) and chromosomal DNA were used as PCR polymerase and PCR template, respectively. The yielded PCR fragment was cloned into pCR2.1-TOPO. As a result of restriction and sequencing analysis, it was found that the clone which the had correct sequence was obtained. One clone was selected for further study (pAMY 1113).

3) Construction of an Expression Vector for the AST Gene Which Functioned in *Phaffia rhodozyma*

An expression plasmid for the AST gene was constructed by restriction digestion and ligation of each genetic component. At first, a 0.3 kb KpnI/PstI fragment from pTPIT1104 and 1.7 kb SacI/KpnI fragment from pG418Sa5112 were ligated into a pGEM-T plasmid which was digested by SacI and PstI. It was found that 9 clones among 12 transformants had correct structure as a result of restriction digestion and one of those was selected for further study (pTPITG1120).

Next, PCR cloning of the AST gene was performed to add the appropriate restriction site to both ends. PCR primers whose sequences are listed in TABLE 13 were synthesized.

Table 13

PCR primers used to clone the entire AST gene cassette
ast11:
TCTAGAATGTTCATCTTGGTCTTGCTCA (sense primer) (SEQ ID NO: 29)
ast12:
CCTGCAGGTCATTCGACCGGCTTGACCT (antisense primer) (SEQ ID NO: 30)

PCR conditions were as follows: 25 cycles of 15 seconds at 94° C., 30 seconds at 55° C. and 2 minutes at 72° C. HF polymerase (Clontech) and pAST1207 were used as PCR polymerase and PCR template, respectively. The yielded PCR fragment was cloned into pCR2.1-TOPO. As a result of restriction and sequencing analysis, it was found that one clone which had correct sequence was obtained. This clone was selected for further study (pAST 113).

Finally, a 1.6 kb SacII/NotI fragment from pAMY1113, a 0.3 kb NotI/XbaI fragment from pTPIP1104 and a 1.5 kb XbaI/Sse83871 fragment from pAST113 were ligated into pTPITG1120 which was digested by SacII and Sse83871. It was confirmed that all five transformants tested had correct structure as a result of restriction analysis. One transformant was selected for further study (pAATG123).

4) Restoration of Astaxanthin Production in Beta-carotene-producing *Phaffia rhodozyma*

The expression plasmid for the AST gene (pAATG123) was transformed into beta-carotene-producing *Phaffia rhodozyma* ATCC96815. Biolistic transformation was performed as described in Example 3. Two geneticin-resistant colonies which colored red were picked up and selected for further study. In order to confirm the integration at the AMY locus on the chromosome of *P. rhodozyma*, a PCR primer whose sequence is listed in TABLE 14 was synthesized.

Table 14

PCR primer used to confirm the integration of expression plasmid at AMY locus on the chromosome of *P. rhodozyma* amy5:

CTCTCCTGTTCACAAAAACA (sense primer) (SEQ ID NO: 31)

Chromosomal DNA was prepared from those transformants and used as a PCR template. PCR condition were as follows: 25 cycles of 15 seconds at 94° C., 30 seconds at 55° C. and 2 minutes at 72° C. ExTaq polymerase (Takara Shuzo) was used as PCR polymerase. A positive 2.0 kb PCR band was yielded in the PCR reaction in which the chromosome obtained from the red-colored transformants was used as a template DNA. No PCR band was observed in the PCR reaction mixture in which chromosome derived from host strain, *P. rhodozyma* ATCC96815 was used as a PCR template.

5) Flask Fermentation By Recombinants in Which the Recombinant AST Gene Was Integrated on the Chromosome of Beta-carotene-producing *P. rhodozyma*

The productivity of astaxanthin was evaluated in the flask fermentation. The medium formulation for flask fermentation is as follows.

TABLE 15

Seed medium formulation for flask fermentation

| | |
|---|---|
| Glucose | 30.0 g/l |
| NH$_4$Cl | 4.83 g/l |
| KH$_2$PO$_4$ | 1.0 g/l |
| MgSO$_4$-7H$_2$O | 0.88 g/l |
| NaCl | 0.06 g/l |
| CaCl$_2$-2H$_2$O | 0.2 g/l |
| KH phthalate | 20.0 g/l |
| FeSO$_4$-7H$_2$O | 28 mg/l |
| Citric acid-1H$_2$O | 15.0 mg/l |
| ZnSO$_4$-7H$_2$O | 40.0 mg/l |
| CuSO$_4$-5H$_2$O | 0.75 mg/l |
| MnSO4-4,5H$_2$O | 0.6 mg/l |
| H$_3$BO$_3$ | 0.6 mg/l |
| Na$_2$MoO$_4$-2H$_2$O | 0.6 mg/l |
| KI | 0.15 mg/l |
| Myo-inositol | 60.0 mg/l |
| Nicotinic acid | 3.0 mg/l |
| Ca D-pantothenate | 3.0 mg/l |
| Vitamin B1 (thiamin HCl) | 3.0 mg/l |
| p-Aminobenzoic acid | 1.8 mg/l |
| Vitamin B6 (pyridoxine HCl) | 0.3 mg/l |
| Biotin | 0.048 mg/l |
| 7 ml/Test Tube (21 mm diameter) | |

TABLE 16

Medium formulation for flask fermentation

| | |
|---|---|
| MgSO$_4$-7H$_2$O | 2.1 g/l |
| CaCl$_2$-2H$_2$O | 0.865 g/l |
| (NH$_4$)$_2$SO$_4$ | 3.7 g/l |
| FeSO$_4$-7H$_2$O | 0.28 g/l |
| Glucose (sterilized separately) | 22 g/l |
| KH$_2$PO$_4$ (sterilized separately) | 14.25 g/l |
| Citric acid-1H$_2$O | 0.21 g/l |
| ZnSO$_4$-7H$_2$O | 70.14 mg/l |
| CuSO$_4$-5H$_2$O | 10.5 mg/l |
| MnSO4-4,5H$_2$O | 8.4 mg/l |
| H$_3$BO$_3$ | 8.4 mg/l |
| Na$_2$MoO$_4$-2H$_2$O | 8.4 mg/l |
| KI | 2.1 mg/l |
| Myo-inositol | 0.374 g/l |
| Nicotinic acid | 18.7 mg/l |
| Ca D-pantothenate | 28.05 mg/l |
| Vitamin B1 (thiamin HCl) | 18.7 mg/l |
| p-Aminobenzoic acid | 11.22 mg/l |
| Vitamin B6 (pyridoxine HCl) | 1.87 mg/l |
| Biotin | 1.122 mg/ |
| CaCO3 | 10 g/l |

1 drop of Actcol (Takeda Chemical Industries Ltd., Osaka, JAPAN) was added to each flask.

50 ml (final volume with 5% of seed inoculum) was added per 500 ml flask with buffles Cells were harvested from fermented broth after a 7-day fermentation and analyzed for their accumulation of astaxanthin and beta-carotene by HPLC as described in Example 4. Results are summarized in TABLE 17.

TABLE 17

Restoration of astaxanthin production by the recombinants in which the AST gene was integrated. (Data is indicated as relative titer of astaxanthin and beta-carotene against the titer of beta-carotene accumulated by *P. rhodozyma* ATCC96815)

| | Relative titer (%) | |
|---|---|---|
| Strain | Astaxanthin | Beta-carotene |
| ATCC96815 :: pR16 | 34.0% | 18.6% |
| ATCC96815 :: pAATG123 | 16.3% | 56.3% |
| ATCC96815 | 0% | 100% |

Partial restoration of astaxanthin production by ATCC96815::pAATG123 indicated that promoter strength by TPI promoter is not strong enough for perfect restoration of astaxanthin production.

The invention being thus described, it will be obvious that the same may be varied in many ways. Such variations are not to be regarded as a departure from the spirit and scope of the invention and all such modifications are intended to be included within the scope of the following claims.

What is claimed is:

1. An isolated polynucleotide encoding 4n enzyme derived from P. rhodozyma and having astaxanthin synthetase activity which enzyme catalyzes the reaction of beta-carotene to astaxanthin.

2. An isolated polynucleotide according to claim 1 which is selected from
   (a) a nucleotide sequence which encodes an enzyme having the amino acid sequence shown in SEQ ID NO: 1, or
   (b) a nucleotide sequence which hybridizes to the complement of a nucleotide sequence which encodes SEQ ID NO:1 under the following hybridization conditions: 50% v/v formamide, 5×SSC, 2% w/v blocking agent, 0.1% N-lauroylsarcosine, 0.3% SDS it 42° C. overnight and which hybrid has astaxanthin synthetase activity.

3. An isolated polynucleotide according to claim 1 which is selected from the group consisting of:
   (i) SEQ ID NO: 2;
   (ii) a nucleotide sequence which, because of the degeneracy of the genetic code, encodes an astaxanthin synthetase having the same amino acid sequence as that encoded by SEQ ID NO:2; and
   (iii) a nucleotide sequence which hybridizes to the complement of the nucleotide sequence from i) or ii) under standard hybridizing conditions (50% v/v formamide, 5×SSC, 2% w/v blocking agent, 0.1% N-lauroylsarcosine, 0.3% SDS at 42° C. overnight).

4. A isolated polynucleotide according to claim 1 which is selected from the group consisting of:
   (i) SEQ ID NO: 3;
   (ii) a nucleotide sequence which, because of the degeneracy of the genetic code, encodes an astaxanthin synthetase having the same amino acid sequence as that encoded by SEQ ID NO:3; and
   (iii) a nucleotide sequence which hybridizes to the complement of the nucleotide sequence from i) or ii) under standard hybridizing conditions (50% v/v formamide, 5×SSC 2% w/v blocking agent, 0.1% N-lauroylsarcosine, 0.3% SDS at 42° C. overnight).

5. A vector or plasmid comprising a polynucleotide which encodes an enzyme derived from P. rohodozyma having astaxanthin synthase activity which catalyzes the reaction of beta-carotene to astaxanthin.

6. A vector or plasmid according to claim 5 wherein the polynucleotide encodes SEQ ID NO:1.

7. A vector or plasmid according to claim 5 wherein the polynucleotide is SEQ ID NO:2.

8. A vector or plasmid according to claim 5 wherein the polynucleotide is SEQ ID NO:3.

9. A host cell transformed or transfected with a polynucleotide which encodes an enzyme derived from P. rhodozyma having astaxanthin synthase activity.

10. A host cell according to claim 9 wherein the polynucleotide encodes a polypeptide having the sequence of SEQ ID NO:1.

11. A host cell according to claim 9 wherein the polynucleotide is SEQ ID NO:2.

12. A host cell according to claim 9 wherein the polynucleotide is SEQ ID NO:3.

13. A host cell according to claim 9 which is transfected or transformed with a vector or a plasmid comprising: (a) a polynucleotide which encodes the polypeptide of SEQ ID NO:1; (b) SEQ ID NO:2; or (c) SEQ ID NO:3.

14. A process for producing a polypeptide derived from *P. rhodozyma* having astaxanthin synthase activity comprising culturing a host cell transformed with a polynucleotide which encodes an enzyme having astaxanthin synthase activity under conditions conductive to produce the enzyme.

15. A process according to claim 14 wherein the polynucleotide encodes the polypeptide of SEQ ID NO:1.

16. A process according to claim 14 wherein the polynucleotide is SEQ ID NO:2.

17. A process according to claim 14 wherein the polynucleotide is SEQ ID NO:3.

18. An isolated polynucleotide encoding a polypeptide which is SEQ ID NO:1.

19. An isolated polynucleotide consisting of SEQ ID NO:2.

20. An isolated polynucleotide consisting of SEQ ID NO:3.

21. A recombinantly-produced polypeptide having astaxanthin synthase activity which is SEQ ID NO:1.

22. A host cell transformed with the vector of claim 21.

* * * * *

UNITED STATES PATENT AND TRADEMARK OFFICE
CERTIFICATE OF CORRECTION

PATENT NO. : 6,365,386 B1 Page 1 of 1
DATED : April 2, 2002
INVENTOR(S) : Tatsuo Hoshino et al.

It is certified that error appears in the above-identified patent and that said Letters Patent is hereby corrected as shown below:

Column 51,
Line 43, please change "4n" to -- an --;
Line 56, please change "it" to -- at --;

Signed and Sealed this

Nineteenth Day of November, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO. : 6,365,386 B1  Page 1 of 1
APPLICATION NO. : 09/518386
DATED : April 2, 2002
INVENTOR(S) : Tatsuo Hoshino et al.

It is certified that error appears in the above-identified patent and that said Letters Patent is hereby corrected as shown below:

Column 51,
Lines 44-45, 58 and 64, please change "synthetase" to -- synthase --;

Column 52,
Lines 47, 51 and 64, please change "3" to -- 4 --;
Line 50, please change "synthetase" to -- synthase --;

Column 53,
Lines 7 and 11, please change "3" to -- 4 --; and

Column 54,
Lines 6 and 11, please change "3" to -- 4 --.

Signed and Sealed this

Fourth Day of July, 2006

JON W. DUDAS
*Director of the United States Patent and Trademark Office*